(12) United States Patent
Gotch

(10) Patent No.: US 9,097,622 B2
(45) Date of Patent: Aug. 4, 2015

(54) PROCESS INTERFACE VALVE ASSEMBLY

(75) Inventor: James E. Gotch, Kirtland, OH (US)

(73) Assignee: Swagelok Company, Solon, OH (US)

( * ) Notice: Subject to any disclaimer, the term of this patent is extended or adjusted under 35 U.S.C. 154(b) by 292 days.

(21) Appl. No.: 13/640,149

(22) PCT Filed: Apr. 15, 2011

(86) PCT No.: PCT/US2011/032638
§ 371 (c)(1),
(2), (4) Date: Oct. 9, 2012

(87) PCT Pub. No.: WO2011/130601
PCT Pub. Date: Oct. 20, 2011

(65) Prior Publication Data
US 2013/0025725 A1    Jan. 31, 2013

Related U.S. Application Data

(60) Provisional application No. 61/324,516, filed on Apr. 15, 2010.

(51) Int. Cl.
*F16K 11/22* (2006.01)
*G01N 1/20* (2006.01)
(Continued)

(52) U.S. Cl.
CPC .............. *G01N 1/2035* (2013.01); *F16K 11/20* (2013.01); *F16K 27/065* (2013.01); *F16K 35/14* (2013.01); *F16K 11/22* (2013.01); *G01N 2001/205* (2013.01)

(58) Field of Classification Search
CPC ....................................... F16K 11/22

USPC ........ 137/637, 637.1, 613; 73/863.85, 863.86
See application file for complete search history.

(56) References Cited

U.S. PATENT DOCUMENTS 1,944,456 A * 1/1934 Pearson ......................... 137/271
3,303,866 A * 2/1967 Ray .................................. 431/54
(Continued)

FOREIGN PATENT DOCUMENTS

| CN | 201166178 | 12/2008 |
|----|-----------|---------|
| GB | 1333499   | 10/1973 |

OTHER PUBLICATIONS

International Search Report and Written Opinion from PCT/US11/32638 dated Jun. 30, 2011.

(Continued)

*Primary Examiner* — John K Fristoe, Jr.
*Assistant Examiner* — Christopher Ballman
(74) *Attorney, Agent, or Firm* — Calfee, Halter & Griswold LLP

(57) ABSTRACT

A valve assembly includes a valve body having a fluid access passage extending from a process fluid port to an access port, a block valve disposed in the fluid access passage and movable between open and closed conditions, an access blocking device disposed in the fluid access passage between the access port and the block valve, and a valve interlock arrangement. The access blocking device is movable from an access blocking condition in which access to the block valve through the access port is blocked, to an access permitting condition in which access to the block valve through the access port is permitted. The valve interlock arrangement is configured such that the block valve is prevented from being moved to the closed condition when the access blocking device is in the access permitting condition.

23 Claims, 26 Drawing Sheets

(51) Int. Cl.
*F16K 27/06* (2006.01)
*F16K 35/14* (2006.01)
*F16K 11/20* (2006.01)

(56) References Cited

U.S. PATENT DOCUMENTS

| | | | |
|---|---|---|---|
| 3,691,846 | A | 9/1972 | Ingold |
| 3,792,612 | A * | 2/1974 | Lammel et al. ............ 73/864.34 |
| 4,108,174 | A | 8/1978 | Slivenko |
| 4,246,115 | A | 1/1981 | Swank |
| 4,294,124 | A * | 10/1981 | Kalwaitis .................... 73/863.85 |
| 4,429,711 | A * | 2/1984 | Schomer ....................... 137/385 |
| 4,841,787 | A * | 6/1989 | Waterman .................... 73/866.5 |
| 4,890,643 | A * | 1/1990 | Oliver ....................... 137/614.11 |
| 5,410,920 | A * | 5/1995 | Westwick .................... 73/866.5 |
| 5,413,309 | A | 5/1995 | Giesler |
| 5,425,305 | A | 6/1995 | Mauritz |
| 5,704,398 | A | 1/1998 | Baker |
| 5,770,809 | A | 6/1998 | Waterman |
| 5,931,801 | A | 8/1999 | Burbank et al. |
| 6,220,290 | B1 | 4/2001 | Lomax |
| 6,620,124 | B1 | 9/2003 | Peavey |
| 6,964,517 | B2 | 11/2005 | Welker |
| 2005/0132825 | A1 | 6/2005 | Talutis |
| 2007/0123825 | A1 | 5/2007 | King et al. |
| 2010/0063482 | A1 | 3/2010 | Mansour et al. |

OTHER PUBLICATIONS

Swagelok Double Block and Bleed Valve—with interlocking handle cam discs preventing simultaneous open position for both valves, concept drawing and isometric views (3 pgs) presented by Swagelok Company to potential customer in discussion of potential sale, prior to Apr. 15, 2009.

* cited by examiner

PROCESS INTERFACE VALVE ASSEMBLY

CROSS-REFERENCE TO RELATED APPLICATION

The present application claims priority from U.S. Provisional Application Ser. No. 61/324,516, entitled "PROCESS INTERFACE VALVE ASSEMBLY," filed on Apr. 15, 2010, the entire disclosure of which is fully incorporated herein by reference.

FIELD OF THE INVENTION

The present application relates to valve assemblies. More particularly, in an exemplary embodiment, the application relates to valve assemblies that can be used to sample fluid from a process piping system.

BACKGROUND

Process interface valves are used to sample fluid from process piping systems. The sampled fluid is tested or analyzed. Process piping systems are used in a variety of different markets, including, but not limited to, oil and gas, chemical, petrochemical, and power generation markets.

One existing series of process interface valves is the KENMAC® series of process interface valves available from Swagelok®. For example, the KENMAC® VB04 valves include first and second block valves disposed in a process fluid access passage and a bleed valve disposed in a vent passage that branches off of the fluid access passage. A probe can be inserted through the first and second block valves and into communication with the process fluid. The process fluid is then sampled through the probe and analyzed. A wide variety of existing instrumentation can be used for the analysis of the process fluid.

SUMMARY

According to an aspect of one or more of the inventions, a valve (for example, a process interface valve) may be configured to receive an element (for example, a probe, tool, fluid, or other media) through an access port for delivery of the element through the open valve. To prevent the valve assembly from being inadvertently operated when the element is extending through the valve, an access blocking device may be disposed in the process fluid access passage to selectively block insertion of the element.

In accordance with an embodiment of one or more of the inventions presented in this disclosure, a valve assembly includes a valve body having a fluid access passage extending from a process fluid port to an access port, a block valve disposed in the fluid access passage and movable between open and closed conditions, an access blocking device disposed in the fluid access passage between the access port and the block valve, and a valve interlock arrangement. The access blocking device is movable from an access blocking condition in which access to the block valve through the access port is blocked, to an access permitting condition in which access to the block valve through the access port is permitted. The valve interlock arrangement is configured such that the block valve is prevented from being moved to the closed condition when the access blocking device is in the access permitting condition.

According to another aspect of one or more of the inventions, a valve interlock arrangement may additionally or alternatively be configured to prevent movement of an access blocking device to an access permitting condition when the fluid control valve is in a closed condition, thereby preventing an impact between an element inserted through an access port and a closed valve element.

According to still another aspect of one or more of the inventions, a method is described for preventing damage to a probe insertable into an access port of a process interface valve assembly and through an open block valve of the process interface valve assembly. In one such method, an indication that the probe may have been inserted through the block valve is provided. Operation of the block valve from an open condition toward a closed condition is prevented in response to the indication that the probe may have been inserted into the block valve. In another method, an indication that the block valve is in the closed condition is provided, and operation of a probe blocking device from a probe blocking condition to a probe accepting condition is prevented in response to the indication that the block valve is in the closed condition.

DESCRIPTION OF THE EXEMPLARY EMBODIMENTS

Figure 1A:
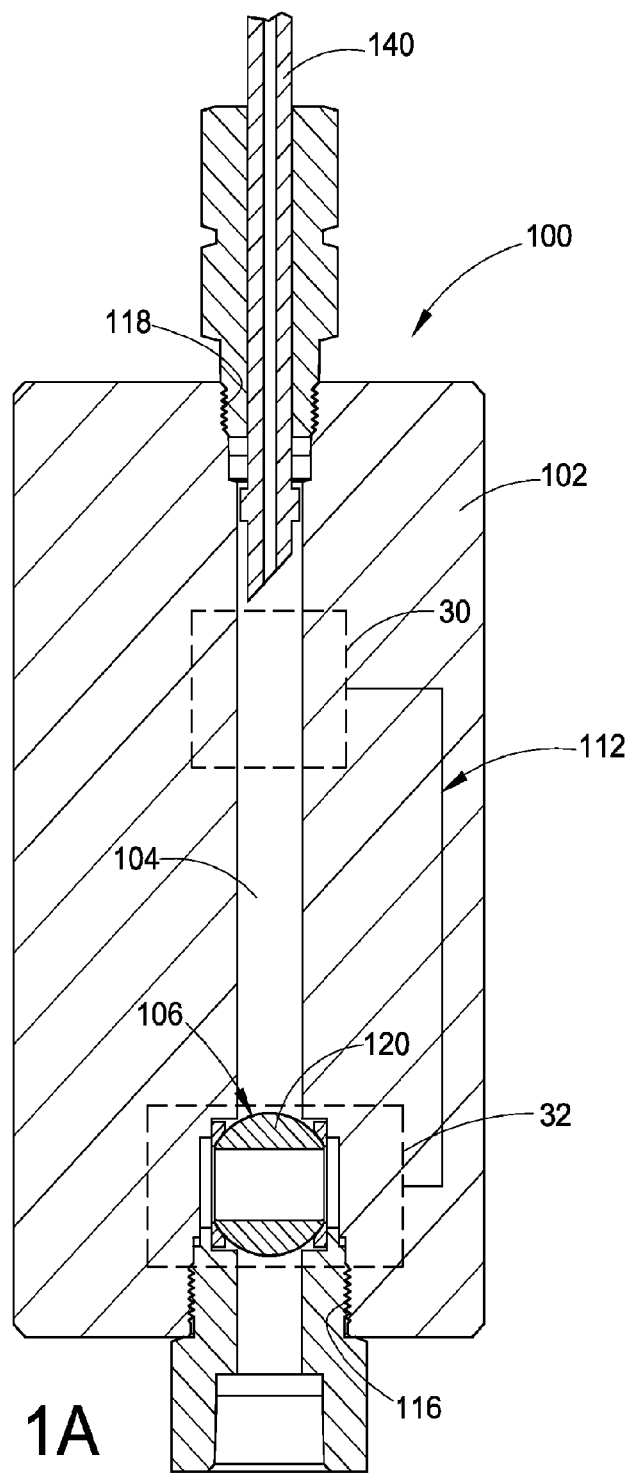
FIG. 1A is a schematic illustration of a process interface valve and interlock assembly with a block valve in a closed position.

While the inventions are described herein with specific reference to a variety of structural and material features, such descriptions are intended to be exemplary in nature and should not be construed in a limiting sense. For example, the exemplary embodiments are described primarily in terms of ball valve assemblies. Those skilled in the art, however, will readily appreciate that any one or more of the aspects and features of the inventions may be used with a valve assemblies that include one or more of a wide variety of different types of valves. Further, the components of the process interface valve assemblies can be made from any suitable materials. For example, all of the components that contact the process fluid can be made from metal, such as stainless steel, carbon steel, duplex steel, or any other metal and/or from polymers, such as plastics (including, for example, PTFE, FEP, PFA, etc.) and elastomers. The materials of the components of the process interface valve assemblies can be selected based on the intended application.

Further, while the exemplary embodiments described herein are identified as process interface valve assemblies for sampling fluid from a process piping system using a probe inserted through the valve assembly, with a mechanical valve interlock preventing rotational closure of a block valve element on the inserted probe, other valve assemblies and systems may utilize one or more of the inventive features described in the present application. For example, a valve assembly may be configured to receive some other tool, medium, or other such element therethrough, for which closure of the valve assembly in this element receiving condition may be undesirable. As another example, a valve interlock arrangement, as used herein, may include any type of arrangement or device configured to restrict or control operation of a first device (such as a block valve or probe blocking device) as a function of a state of a second device (such as a block valve or probe blocking device), such as an operational position of the second device, or the presence of an inserted element within the second device. For example, many types of mechanical, electrical, electromechanical, magnetic, or fluid driven valve interlock arrangements may be utilized to prevent closure of a valve element on an inserted element. As still another example, a mechanical interlock arrangement utilizing one or more of the features described herein may be provided to limit the corresponding conditions of two or more rotationally adjustable devices, including, for example, shut-off valves, multidirectional valves, regulating valves, blocking devices, electrical knobs, and other such devices.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, circuits, devices and components, hardware, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure, however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated.

Figure 1B:
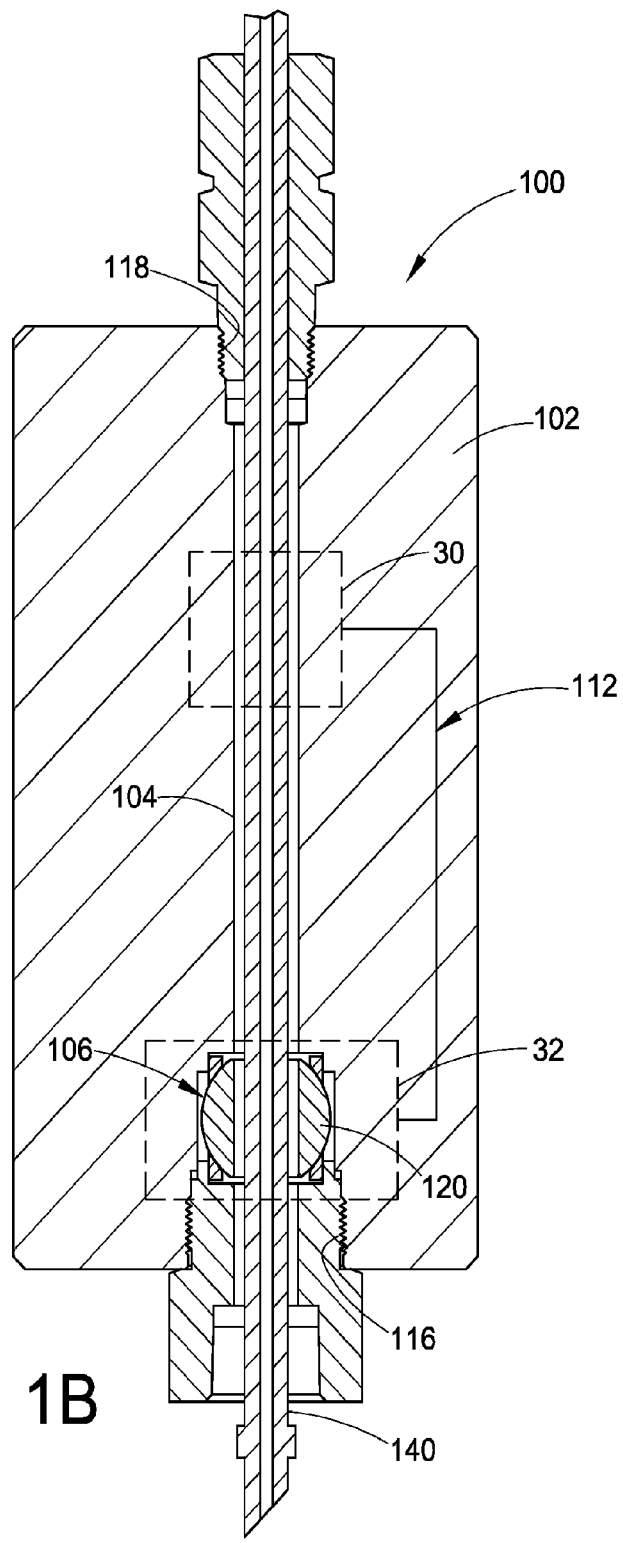
FIG. 1B illustrates the process interface valve and interlock assembly of FIG. 1A with the block valve in an open position and a probe inserted through the block valve.

FIGS. 1A and 1B schematically illustrate an exemplary embodiment of a process interface valve assembly 100 with an exemplary valve interlock arrangement 112. The illustrated process interface valve assembly 100 includes a valve body 102, a process fluid access passage 104, and a block valve 106. The process fluid access passage 104 extends through the valve body 100 from a process fluid port 116 to an access port or probe port 118. The illustrated block valve 106 includes a valve element 120 disposed in the process fluid access passage 104. The block valve 106 is operable to selectively open (see FIG. 1B) and close (see FIG. 1A) the fluid access passage 104.

According to an aspect of the present application, an assembly including first and second devices may be provided with an interlock arrangement configured such that operability of one of the first and second devices is a function of an operational state of the other of the first and second devices. In one embodiment, a valve interlock arrangement associated with a block valve and a probe blocking device is configured such that operability of one of the block valve and the probe blocking device is a function of an operational state of the other of the block valve and the probe blocking device. As one example, the valve interlock arrangement may be configured such that the block valve is prevented from being moved to or toward a closed condition when the probe blocking device is in a probe accepting condition, with the block valve being permitted to move to or toward the closed condition when the probe blocking device is in a probe blocking condition. As another example, the valve interlock arrangement may additionally or alternatively be configured such that the probe blocking device is prevented from being moved to or toward the probe accepting condition when the block valve is in the closed condition, with the probe blocking device being permitted to move to or toward the probe accepting condition when the block valve is in the open condition.

Figure 2:
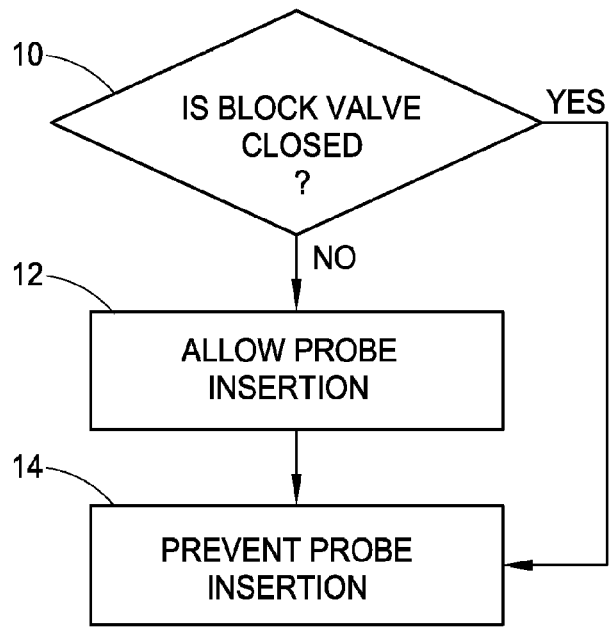
FIG. 2 is a flow chart illustrating operation of a probe access valve interlock assembly.

Referring to FIG. 2, in one exemplary embodiment, the valve interlock arrangement 112 changes state 10 depending on whether the valve is open or the valve is closed. If the valve is open, the valve interlock arrangement 112 allows 12 insertion of a probe 140 through the block valve 106 (see FIG. 1B). If the valve 106 is closed, the valve interlock arrangement 112 prevents 14 insertion of the probe 140 to the block valve. This may inhibit potential damage to the block valve 106 and/or the probe 140.

Figure 3:
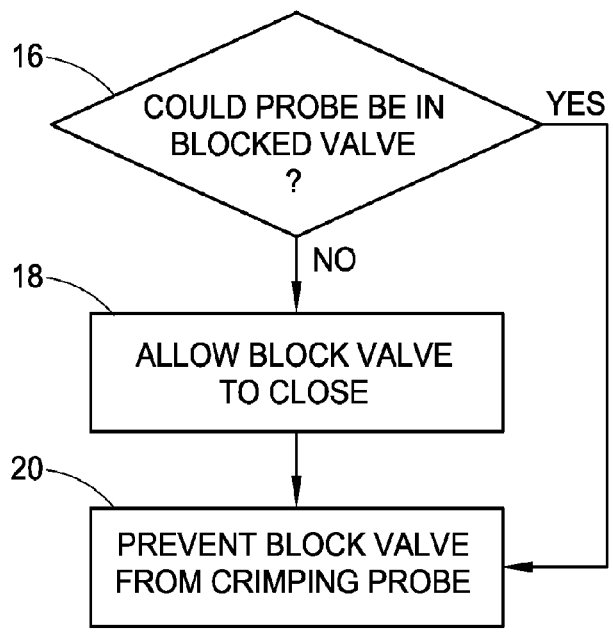
FIG. 3 is a flow chart illustrating operation of a probe access valve interlock assembly.

Referring to FIG. 3, in another exemplary embodiment, the valve interlock arrangement 112 of FIGS. 1A and 1B changes state 16 depending on whether or not the probe 140 could be disposed in the block valve 106. If the probe 140 could not be disposed in the block valve 106, the interlock arrangement 112 allows 18 the block valve 106 to close. If the probe 140 could be disposed in the block valve 106, the interlock arrangement 112 prevents 20 the block valve 106 from closing. This prevents the block valve 106 from potentially crimping or otherwise damaging the probe 140.

In another embodiment, the valve interlock arrangement 112 performs the functions illustrated by FIG. 2 and the functions illustrated by FIG. 3. In this embodiment, the probe 140 is inhibited from being inserted into contact with a closed block valve 106 and a probe in an open block valve is inhibited from being damaged by moving the block valve from the open position toward the closed position.

The valve interlock arrangement 112 may take a wide variety of different forms. For example, any type of sensor may be employed to sense the position of the block valve 106 and/or the probe 140. The output of such a sensor or sensors may be used to control a mechanism that selectively inhibits movement of the probe 140 and/or the block valve 106. The valve interlock arrangement may comprise one or more mechanical linkages that selectively inhibit movement of the block valve 106 based on the position or possible positions of the probe 140 and/or that selectively inhibit movement of the probe based on the position of the block valve. The output of a sensor or sensors may be provided to a controller or computer that automatically controls the valves. The controller or computer may be programmed to selectively inhibit movement of the block valve based on the position or possible positions of the probe 140 and/or that selectively inhibit movement of the probe based on the position of the block valve. Any arrangement that performs one or more of the functions illustrated by FIGS. 2 and 3 can be employed.

In FIGS. 1A and 1B, the valve interlock arrangement 112 is schematically illustrated and includes a probe interface component 30 that is linked to a block valve interface component 32. In one exemplary embodiment, the block valve interface component 32 provides an indication of whether the block valve 106 is open or closed. The probe interface component 30 is linked to the block valve interface component 32, such that the probe interface component 30 allows insertion of the probe when the block valve interface component indicates that the block valve 106 is open and prevents insertion of the probe when block valve interface indicates that the block valve is closed.

In one exemplary embodiment, the probe interface component 30 provides an indication of whether the probe 140 is or could be disposed in the block valve 106. The probe interface component 30 is illustrated as being downstream of the block valve 106, but could be disposed at the block valve 106 or any other suitable location. The block valve interface component 32 is linked to the probe interface component 30, such that the block valve interface component 32 inhibits movement of the block valve toward the closed position when the probe is or could be disposed in the block valve and allows the block valve to close when the probe is not or could not be disposed in the block valve.

The probe interface component 30 may take a wide variety of different forms. For example, the probe interface component 30 may be a sensor that provides an indication of the presence or position of the probe. The probe interface component 30 may be a blocking member or mechanism that selectively blocks the process fluid passage 104. In the embodiment represented by FIG. 2, such a blocking member or mechanism would selectively allow or prevent insertion of the probe 140. In the embodiment represented by FIG. 3, such a blocking member or mechanism would provide an indication of whether the probe could be in the block valve, since the probe could not be in the block valve if the process fluid passage is blocked (for example, by an access blocking device).

The valve interface component 32 may take a wide variety of different forms. For example, the valve interface component 32 may be a sensor that provides an indication of the position of the block valve 106 or a component that moves as the valve 106 moves from the open position to the closed position.

Figure 4A:
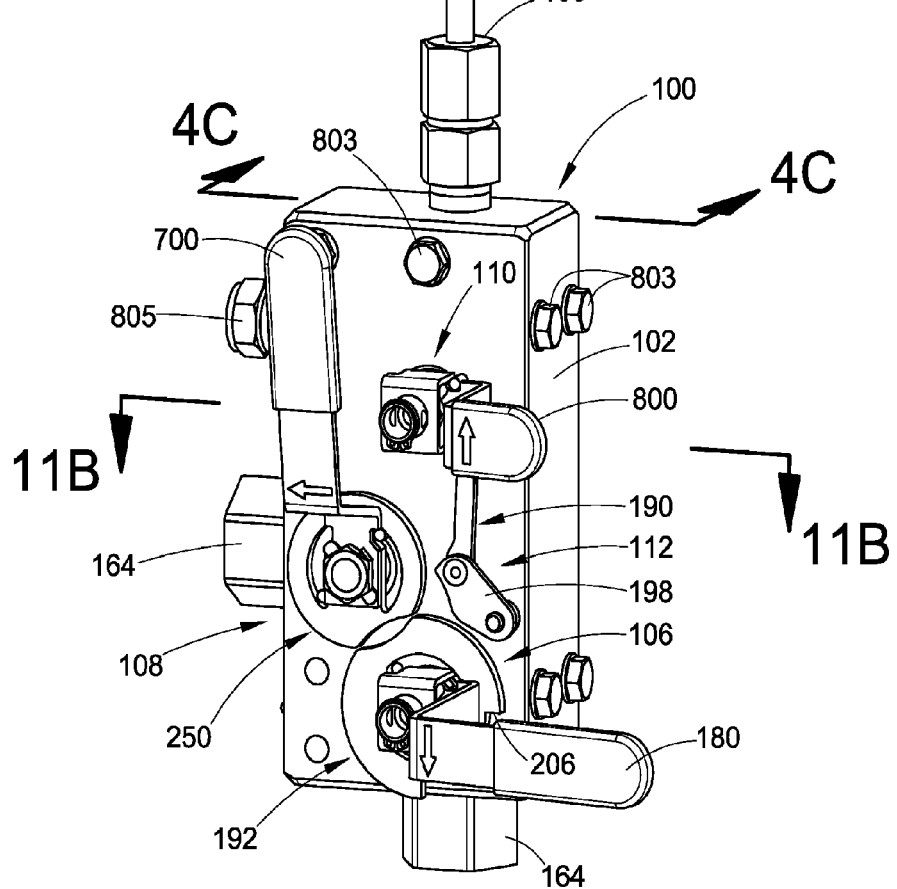
FIG. 4A is a perspective view of an exemplary embodiment of a process interface valve assembly and a probe.
Figure 4B:
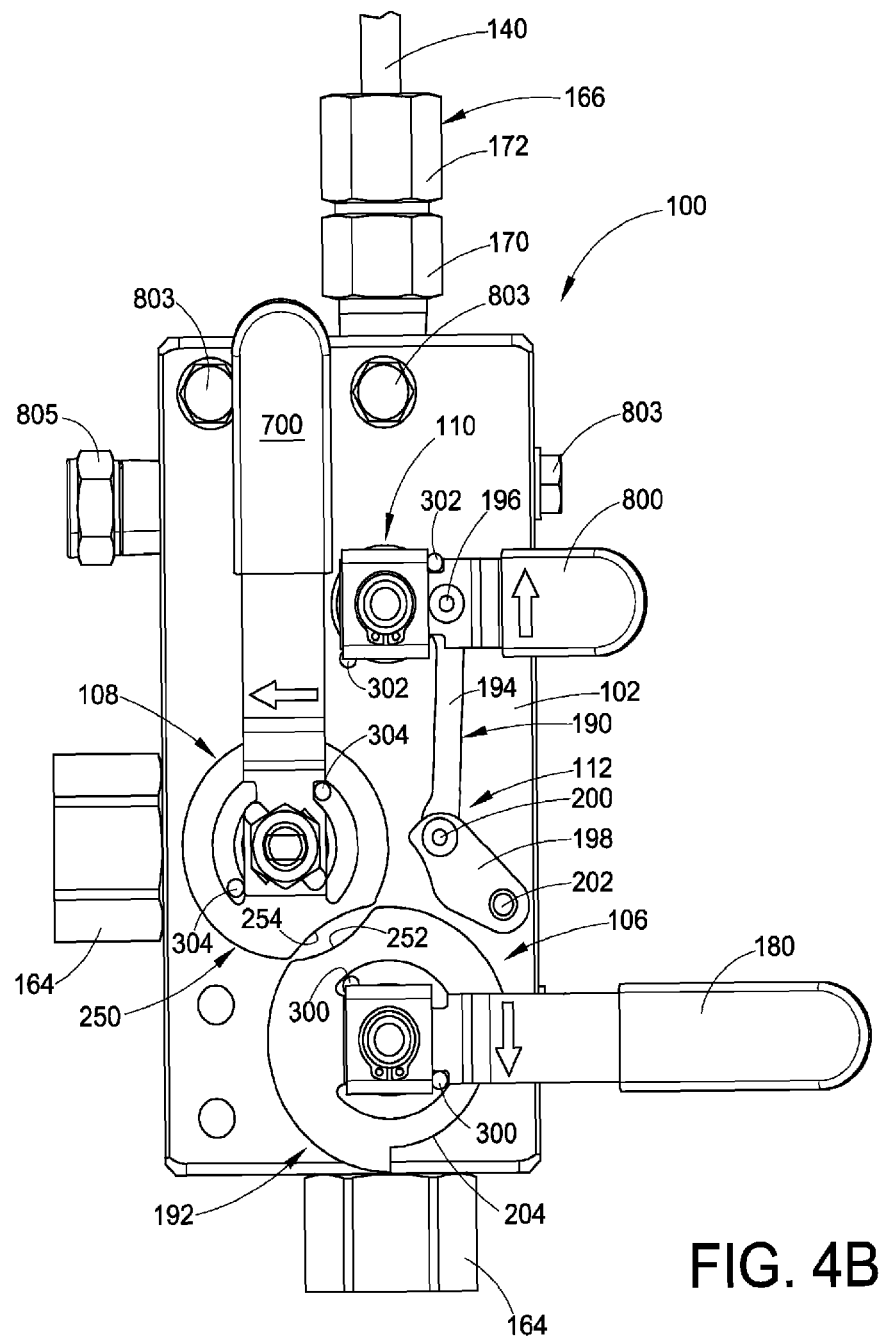
FIG. 4B is an enlarged front view of the process interface valve assembly shown in FIG. 4A.
Figure 4C:
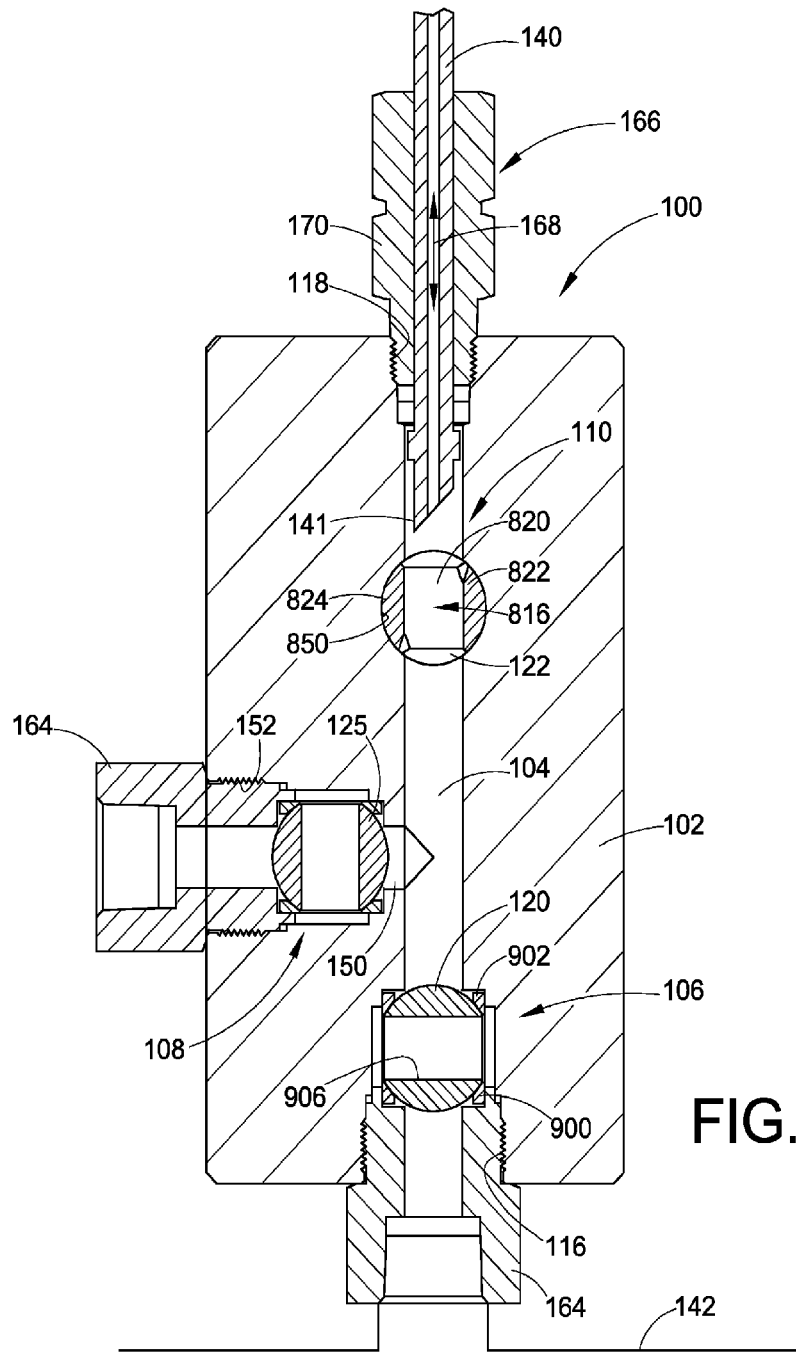
FIG. 4C is an enlarged sectional view taken along the plane indicated by lines 4C-4C in FIG. 4A.

The process interface valve assembly 100 with a valve interlock arrangement 112 can take a wide variety of different forms. FIGS. 4A-4C provide a non-limiting example of a process interface valve assembly 100 that includes an interlock arrangement 112. However, the process interface valve assembly 100 and the valve interlock 112 can take a wide variety of different forms. In the example of FIGS. 4A-4C, process interface valve assembly 100 includes a valve body 102, a process fluid access passage 104 (FIG. 4C), a block valve 106, and an optional bleed valve 108. While the exemplary valve body 102 is shown as a single unitary body in which the block valve 106, bleed valve 108, and probe blocking device 110 are installed, in other embodiments, a valve body may be formed from multiple bodies detachably or permanently assembled with each other. For example, a valve body may be formed from the bodies of separate block valve, bleed valve, and probe blocking devices.

In the example illustrated by FIGS. 4A-4C, the probe interface component 30 (see FIG. 1A) of the valve interlock arrangement 112 comprises an access blocking device or probe blocking device 110. The probe blocking device 110 has a probe blocking member 122 (FIG. 4C) disposed in the process fluid access passage between the probe port 118 and the block valve element 120. The probe blocking device 110 is moveable from an access blocking or probe blocking position where a probe is prevented from being inserted through the probe port 118 past the blocking member 122 of the probe blocking device 110 (see FIG. 4C) to an access permitting or probe accepting position where the probe is insertable through the probe port past the probe blocking device 110 (see FIG. 8).

Figure 7:
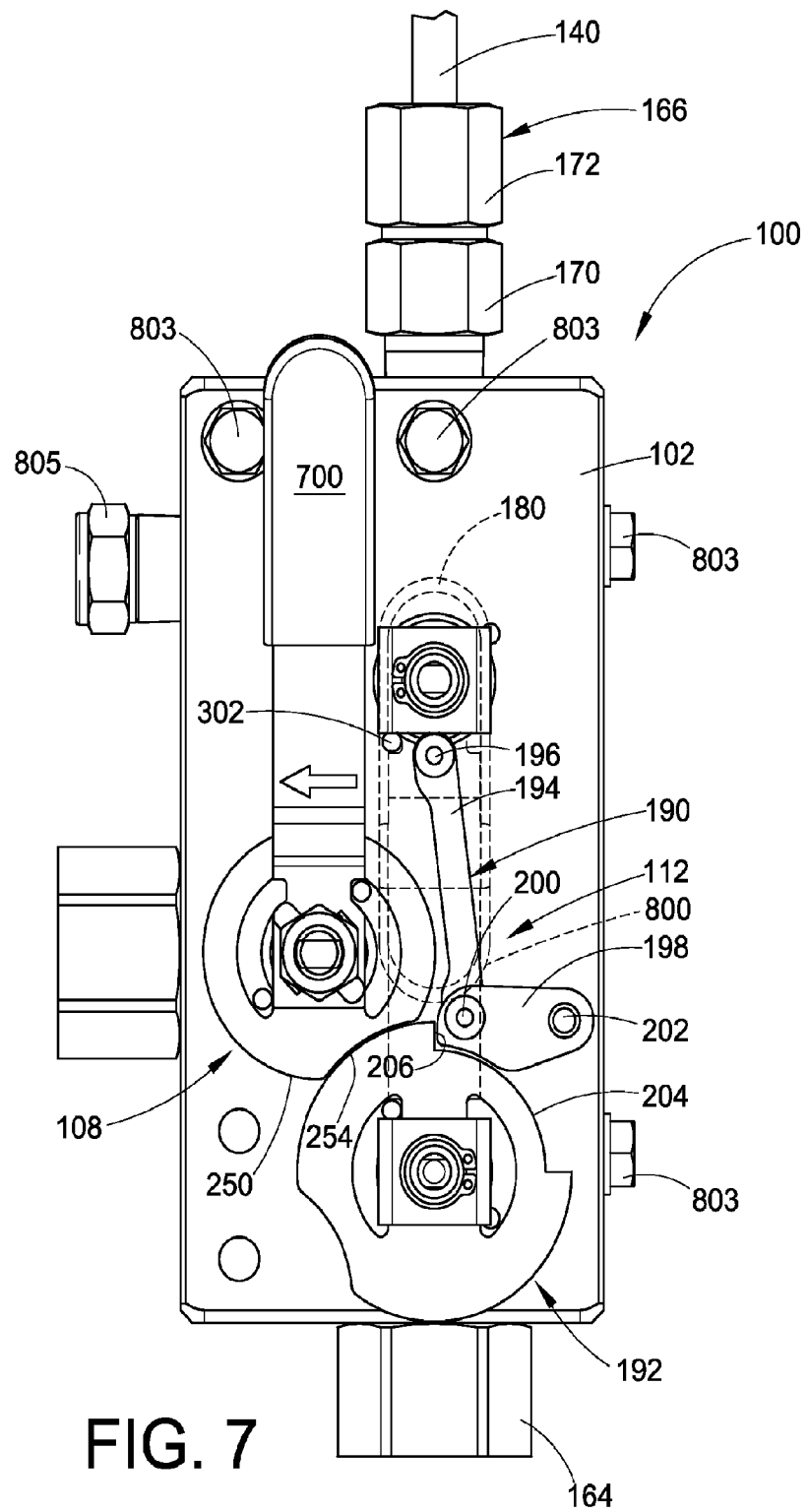
FIG. 7 is a front view of a process interface valve assembly illustrating a probe blocking device moved to a probe accepting position, with the handles of the block valve and probe blocking device shown in phantom to illustrate additional features of the assembly.
Figure 8:
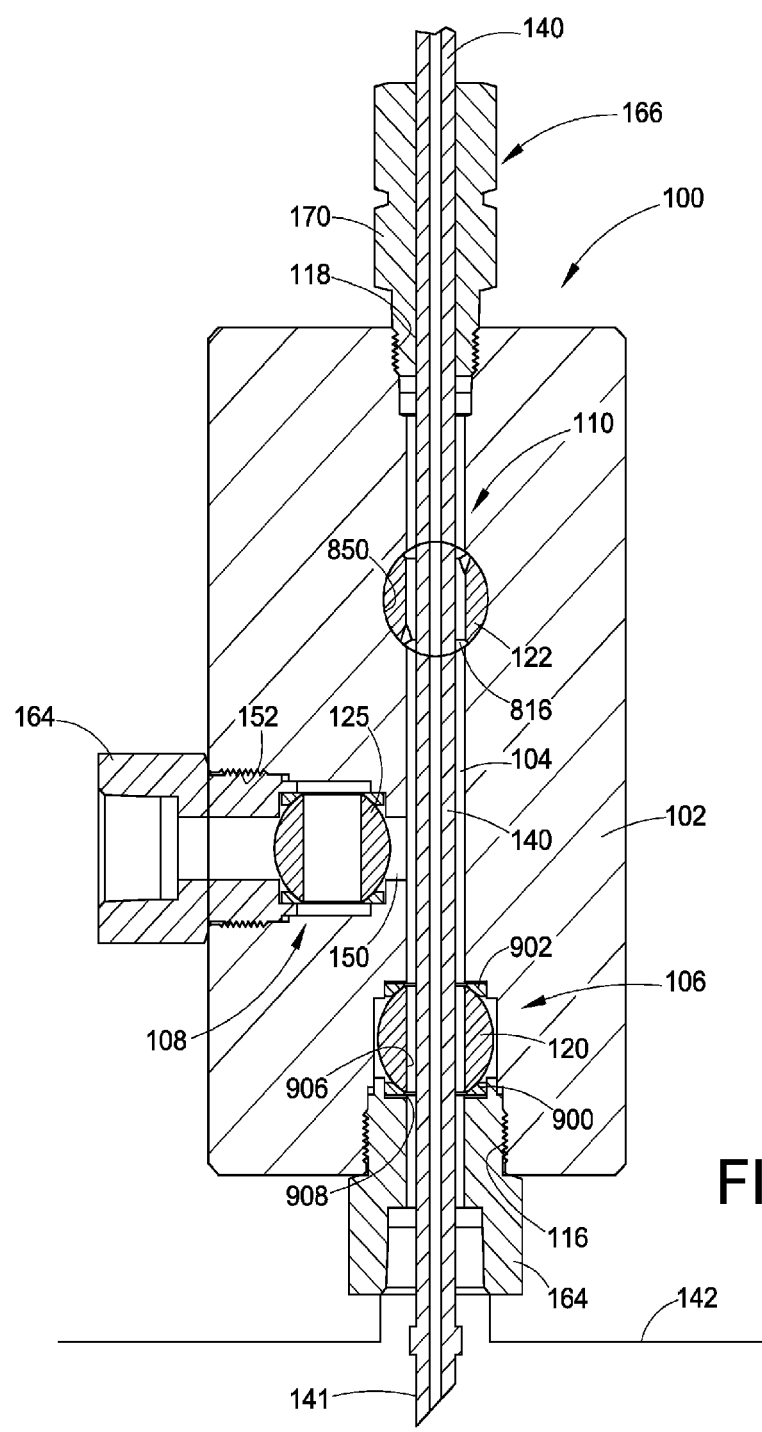
FIG. 8 is an enlarged sectional view of the probe interface valve assembly shown in FIG. 7, with a probe inserted through the probe interface valve assembly.

Referring to FIG. 4C, when the block valve 106 is closed, a process fluid is prevented from flowing in the fluid access passage past the valve element 120. Referring to FIG. 8, when the block valve 106 is open and the probe blocking device 110 is in the probe accepting position 110, a probe 140 can be inserted into a process fluid vessel or conduit 142, such as a pipe. In the illustrated embodiment, the valve interlock arrangement 112 is configured such that the block valve 106 is prevented from being moved from the open position to the closed position when the probe blocking device 110 is in the probe accepting position (see FIG. 7). This prevents the block valve 106 from being closed while the probe 140 is disposed in the valve member 120 of the block valve 106.

Figure 13:
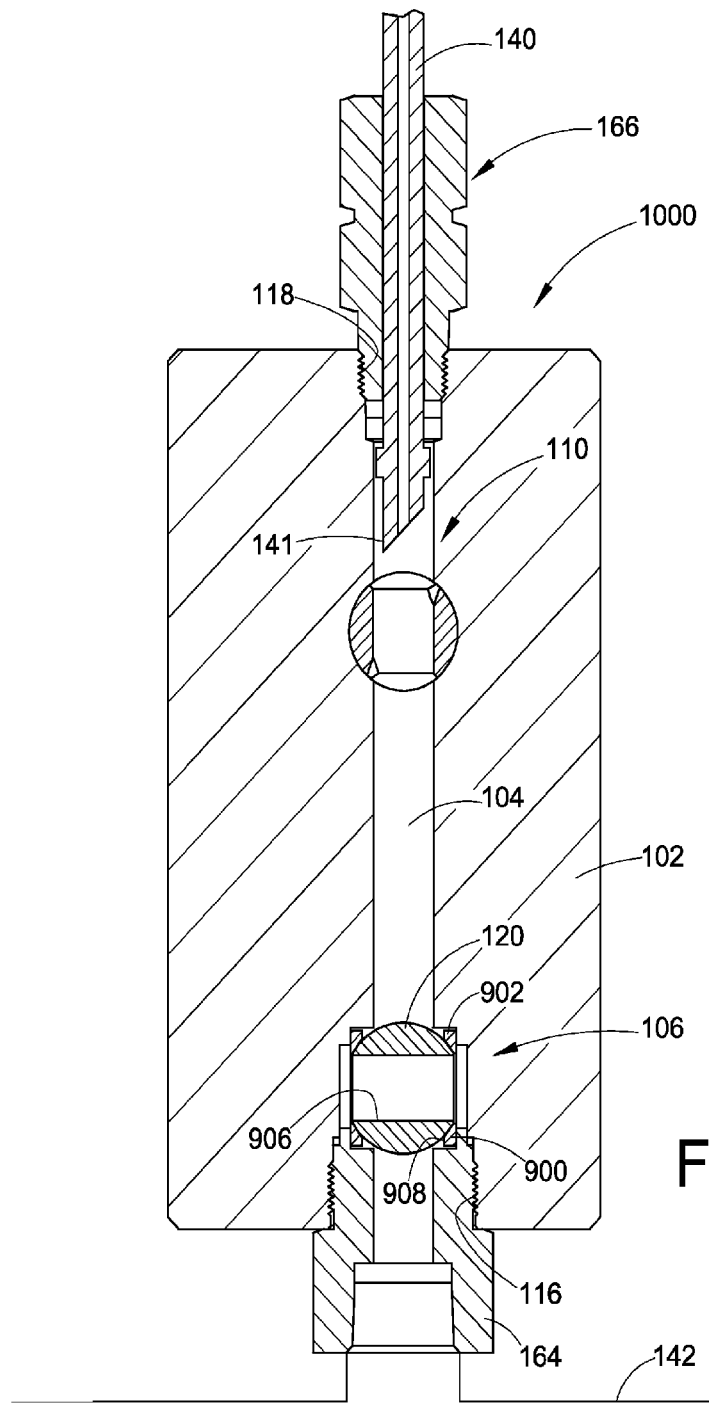
FIG. 13 is a sectional view of an embodiment of another process interface valve assembly.

In the embodiment illustrated by FIGS. 4A-4C, the process interface valve assembly 100 includes the optional bleed valve 108. FIG. 13 illustrates an embodiment of a process interface valve assembly 1000 that does not include the optional bleed valve 108. The process interface valve assembly 1000 is not described in detail, since all of its components are included in the process interface valve assembly 100.

Referring to FIG. 4C, when the optional bleed valve 108 is included, a bleed passage 150 is defined in the valve body 102. The bleed passage 150 extends from a bleed port 152 to the process fluid access passage 104. The bleed valve 108 has a valve element 125 disposed in the bleed passage 150. The bleed valve 108 is operable to selectively open and close the bleed passage 150. In the FIG. 4C example, the valve element 120 of the block valve 106 is disposed between the process fluid port 116 and the bleed passage 150. In the FIG. 4A-4C embodiment, the valve interlock arrangement 112 is configured such that the bleed valve 108 is prevented from being opened when the block valve is open (see FIG. 6A) and the block valve is prevented from being opened when the bleed valve is open (see FIG. 10A).

The valve body 102 can take a wide variety of different forms. Any structure that provides an interface to the process fluid vessel or conduit 142 can be used. In the illustrated embodiment, the fluid access passage 104 is straight. In other embodiments, the fluid access passage may be curved or have a curved portion. For example, the fluid access passage 104 may be curved or have a curved portion if the probe is flexible.

The process fluid port 116 may take a wide variety of different forms. For example, the process fluid port 116 may be any structure configured to couple with any type of fitting capable of coupling the fluid access passage 104 to the process fluid vessel or conduit 142. In the illustrated embodiment, the process fluid port 116 comprises internal threads (see FIG. 4C) that accept an end screw 164.

A wide variety of different types of probes can be used with the process interface valve assembly. The illustrated probe 140 comprises an elongated tube having a first open end 141 with a valve 143 coupled to a second end (see FIG. 4A). The valve 143 can be opened and closed to control fluid flow through the probe. In other embodiments, other insertable elements, such as sensors, cameras, or other tools, or other materials or media, may be used with a valve assembly as described herein.

The access port or probe port 118 may take a wide variety of different forms. For example, the probe port 118 may be any structure configured to couple with any type of fitting 166 capable of accepting and sealing around a probe 140. In an exemplary embodiment, the probe fitting 166 is configured to maintain the seal with the probe 140, when the probe is moved in the process passage 104 as indicated by arrows 168 in FIG. 4C. A wide variety of existing fittings can be used as the probe fitting. In the illustrated embodiment, the probe port comprises internal threads (see FIG. 4C) that accept a first component 170 of the probe fitting 166. A second component 172 of the fitting may be tightened to the first fitting component 170 to form a seal around the probe 140 in a well known manner. For example, tightening the first fitting component 170 with the second fitting component 172 may compress a seal member or packing to form a seal around the probe 140.

The block valve 106 may take a wide variety of different forms. Examples of different types of valves that may be used include, but are not limited to, ball valves, plug valves, shuttle valves, needle valves, gate valves, spool valves and the like. Any type of valve capable of opening and closing the fluid access passage 104 can be used. In an exemplary embodiment, the valve also allows the probe 140 to be inserted past the block valve in the fluid access passage.

Figure 12:
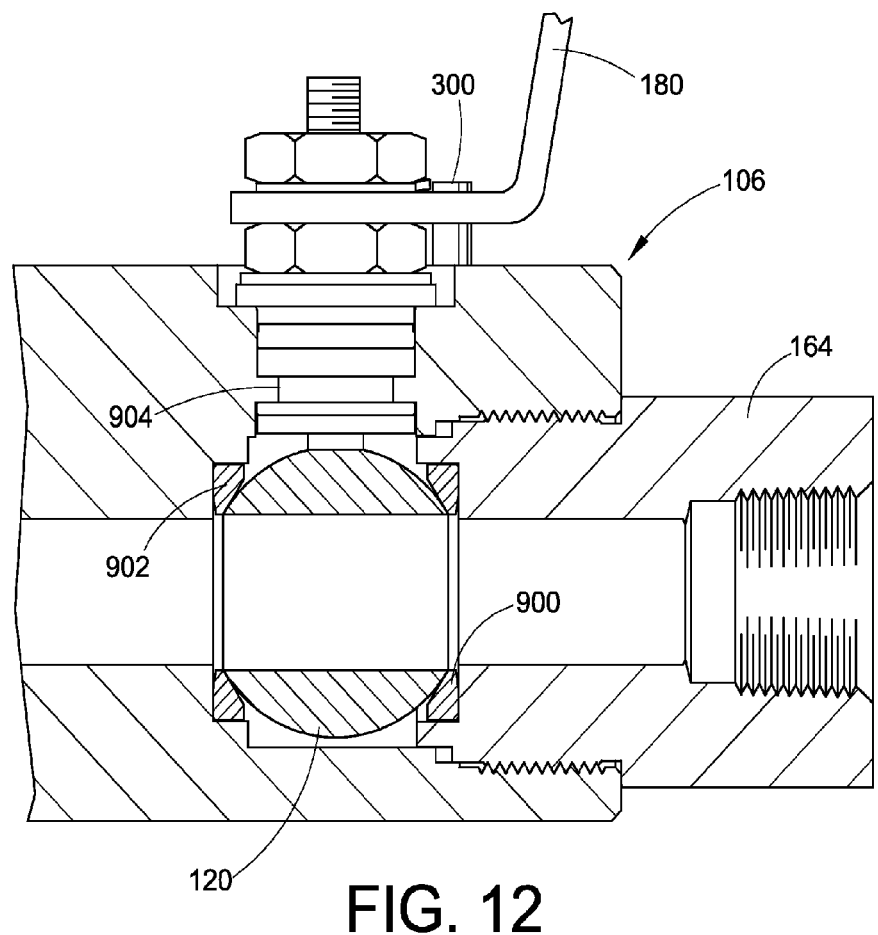
FIG. 12 is a enlarged sectional view showing ball valve components that can be used in the process interface valve.

The illustrated block valve 106 is a ball valve. A wide variety of different ball valve configurations may be used. One suitable ball valve configuration is the configuration of the VB04 ball valve modules of the KENMAC® series of process interface valves available from Swagelok®. FIG. 12 is an enlarged cross-sectional illustration of components of the block valve 106. The block valve 106 includes the valve element 120, a first valve seat 900, a second valve seat 902, and a valve stem 904. The illustrated valve element 120 is spherical and includes a flow passage 906. The illustrated valve seats 900, 902 are annular with a central openings 908. The valve seat 900 seals against the valve element 120 and the end screw 164. The valve seat 902 seals against the valve body 102 and the valve element 120. The valve stem 904 is coupled to the valve element 120 and a block valve handle 180. Rotation of the handle 180 rotates the valve stem 904 to rotate the valve element to the open and closed positions. In the open position, the central openings 908, 910 are aligned with the flow passage 906 to allow fluid flow (see FIG. 6B). In the closed position, the flow passage 906 is misaligned with (or does not overlap with) the central openings 908, 910 to prevent flow (see FIG. 4C).

Figure 6A:
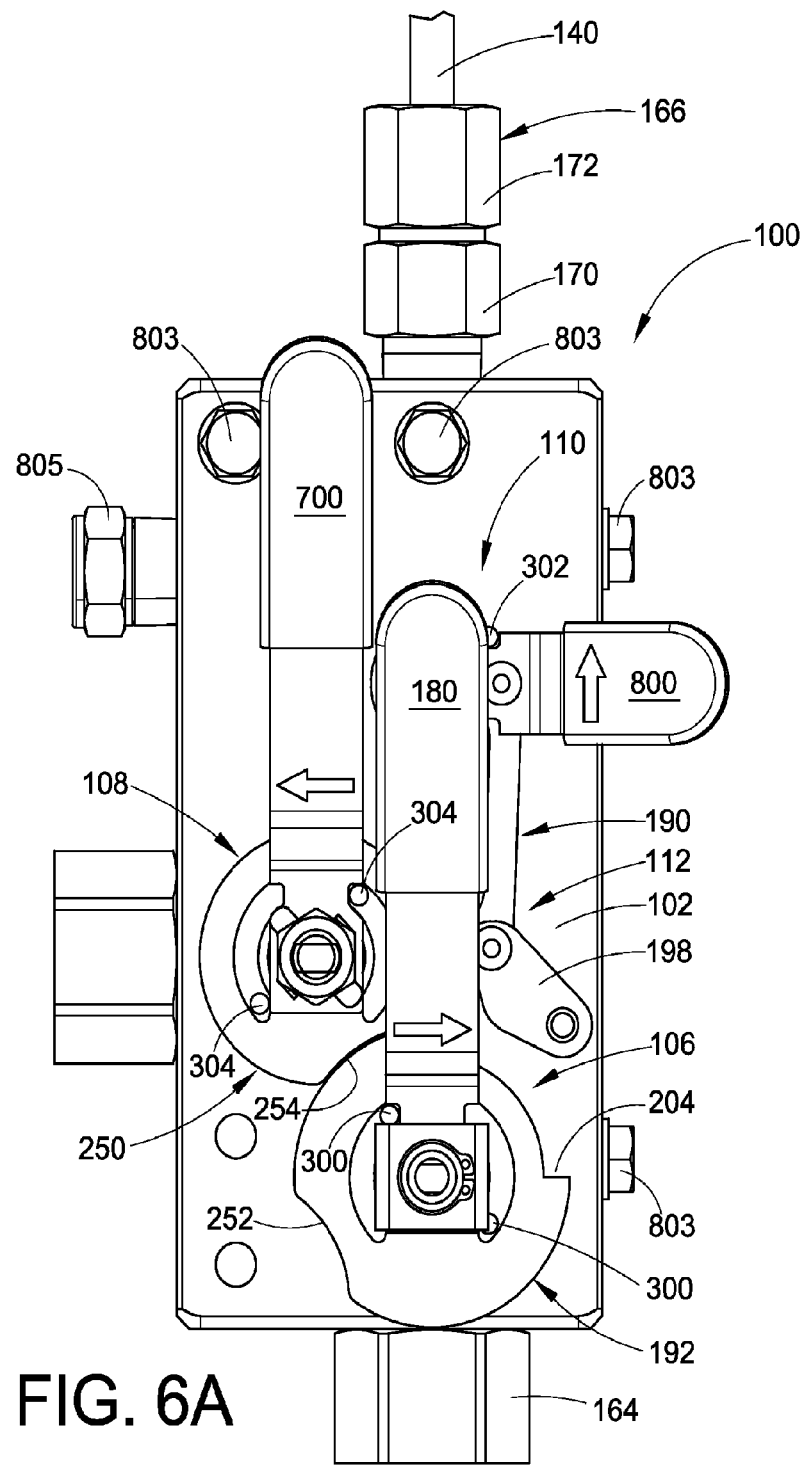
FIG. 6A is a front view of the process interface valve assembly illustrating a block valve moved from a closed position to an open position.

In the illustrated embodiment, the block valve 106 is limited to ninety degrees of rotation between the closed position (see FIG. 4B) and the open position (see FIG. 6A). This can be accomplished in a wide variety of different ways. In the illustrated embodiment, stop pins 300 are disposed in the valve body 102. The stop pins 300 are positioned to engage the block valve handle 180 at the open and closed positions.

The access blocking or probe blocking device 110 can take a wide variety of different forms. Any arrangement capable of selectively preventing and allowing probe insertion to the block valve 106 can be used. The probe blocking device 110 may prevent or allow fluid flow between the probe port 118 and the block valve 106 when the probe blocking device is in the probe blocking position. A valve may be used as the probe blocking device if the probe blocking device 110 is intended to prevent fluid flow between the probe port 118 and the block valve 106 when the probe blocking device is in the probe blocking position. Examples of types of valves that may be used as the probe blocking device 110 include, but are not limited to, ball valves, plug valves, shuttle valves, needle valves, and the like. Examples of types of mechanisms that may be used as the probe blocking device 110 if the probe blocking device is not intended to prevent fluid flow between the probe port 118 and the block valve 106 include, but are not limited to, rotary and/or linear devices having a passage that is selectively alignable with the process fluid passage 104 and devices having blocking portions that are selectively moveable into the process fluid passage, such as devices that include a blocking pin or other blocking member sufficient to obstruct insertion of a probe or other insertable element into the block valve 106.

Figure 11A:
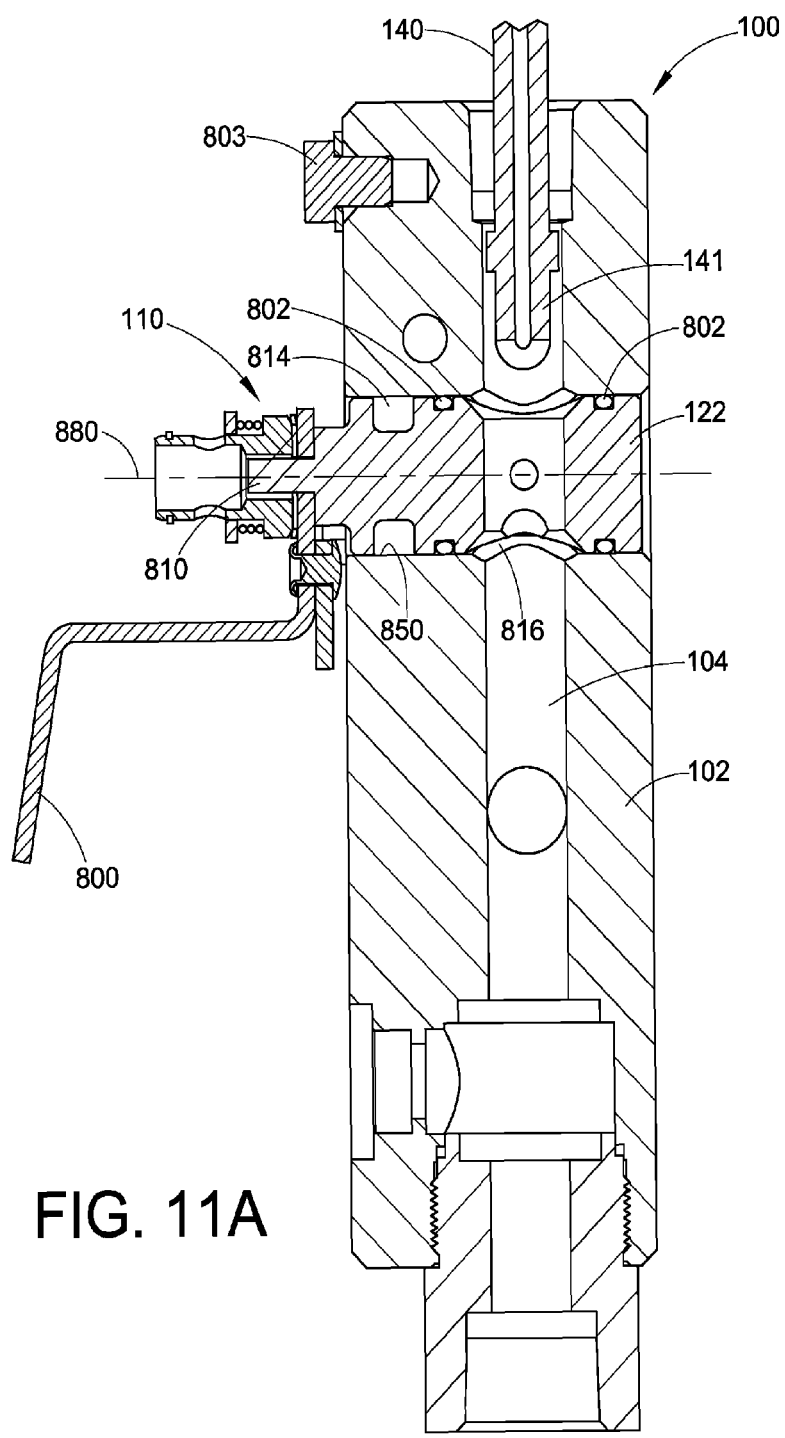
FIG. 11A is a sectional view illustrating components of an exemplary embodiment of a probe blocking device.
Figure 11B:
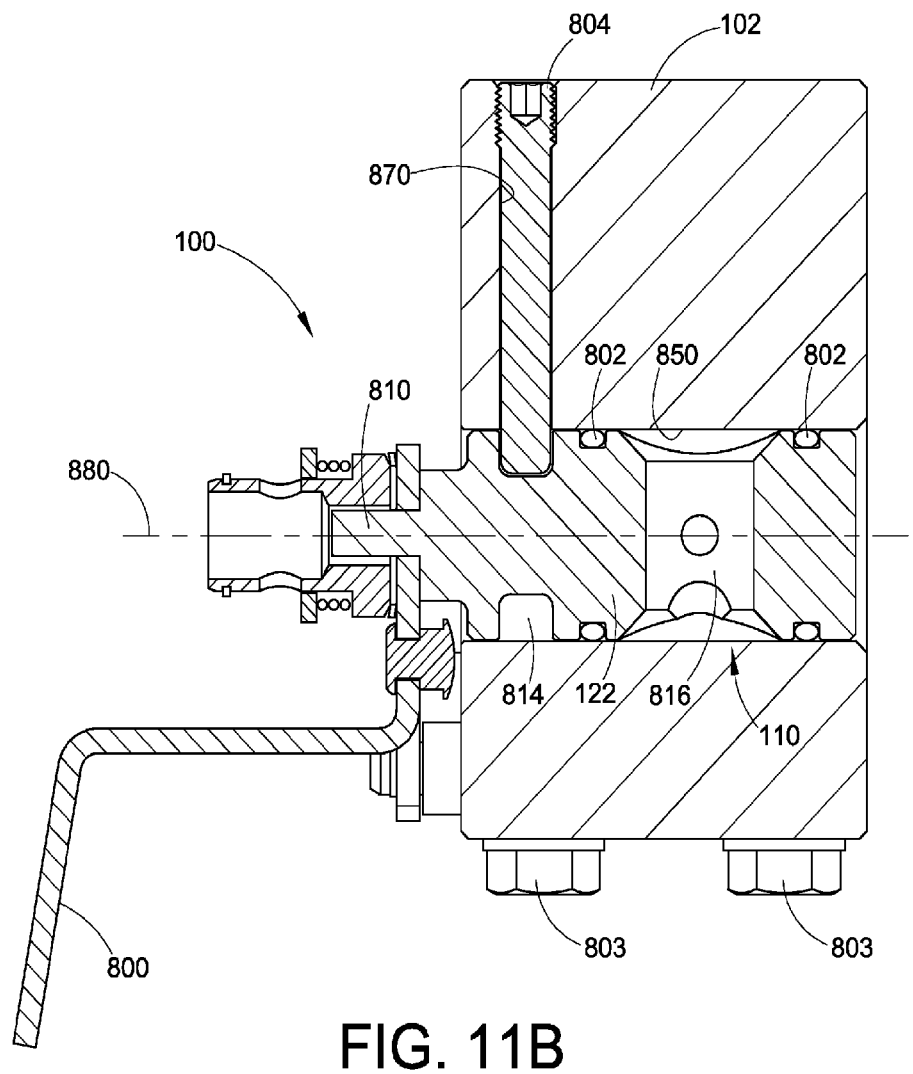
FIG. 11B is another sectional view of the probe blocking device of FIG. 11A.
Figure 11C:
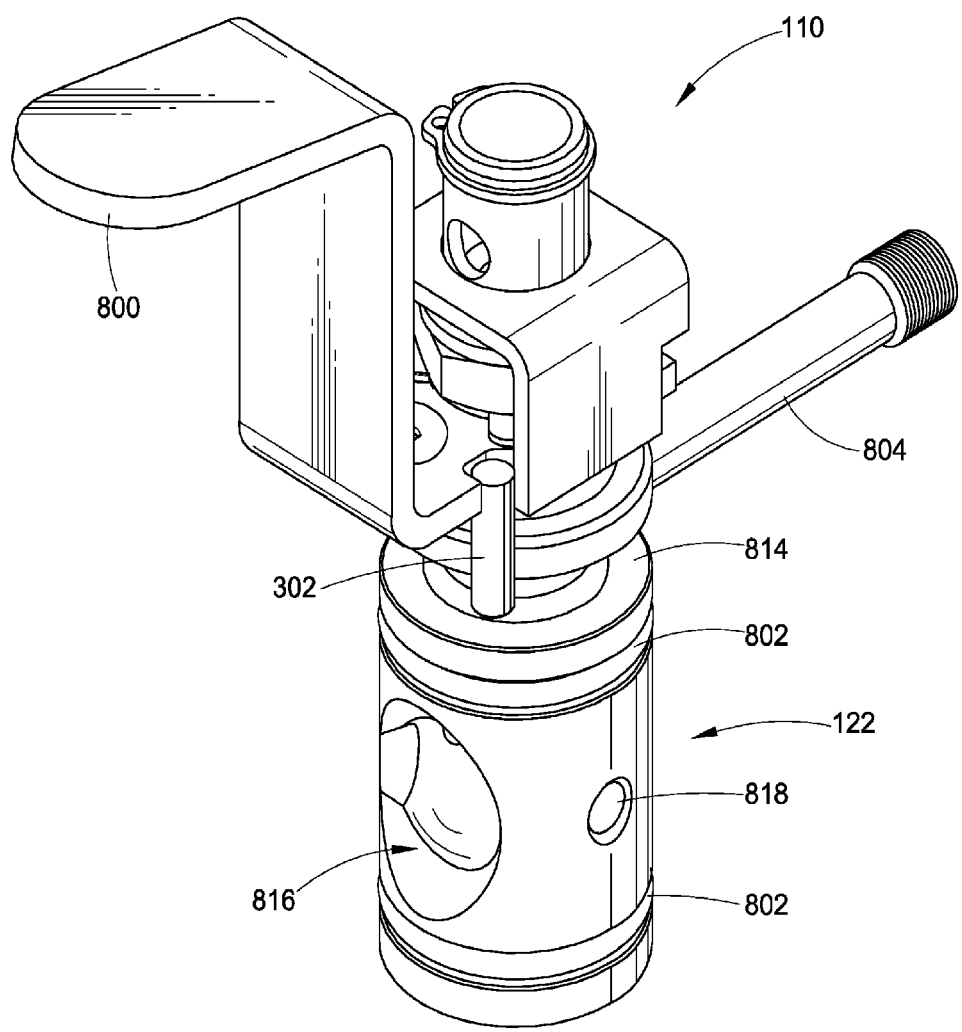
FIG. 11C is a perspective view illustrating components of the probe blocking device of FIG. 11A.

FIGS. 11A-11C are illustrations of an exemplary embodiment of an access blocking or probe blocking device 110. The illustrated probe blocking device 110 includes the probe blocking member 122, a handle 800, seal rings 802, and a retention pin 804. Referring to FIGS. 11A and 11B, the probe blocking member 122 is cylindrical with an integral stem 810. First and second annular seal recesses 812 are defined in the probe blocking member 122. An annular retention recess 814 is defined in the probe blocking member 122. The probe blocking member 122 includes a probe passage 816. The probe passage 816 may take any form that allows the probe 140 to be inserted through the probe blocking member 122. In one exemplary embodiment, the probe passage 816 is configured to reduce stress applied to the probe 140 when the probe blocking device is moved from the probe accepting position toward the probe blocking position to move the probe blocking member 122 into contact with the probe (see FIGS. 9 and 9A). This reduced stress can be accomplished in a variety of different ways. For example, the probe passage can be configured to increase the contact area between the probe blocking member 122 and the probe 140 when the probe blocking device is moved from the probe accepting position toward the probe blocking position. In such an example, notches 822, 824 in the edges of the cylindrical bore 820 may be oriented to provide surface contact between the outer surface of the probe and the edge of the central bore when the probe blocking member is rotated toward the probe blocking condition and into engagement with the inserted probe. This increases the contact area between the probe blocking member 122 and the probe 140 as compared to a substantially continuous cylindrical bore, to reduce the potential stress applied to the probe.

Figure 11D:
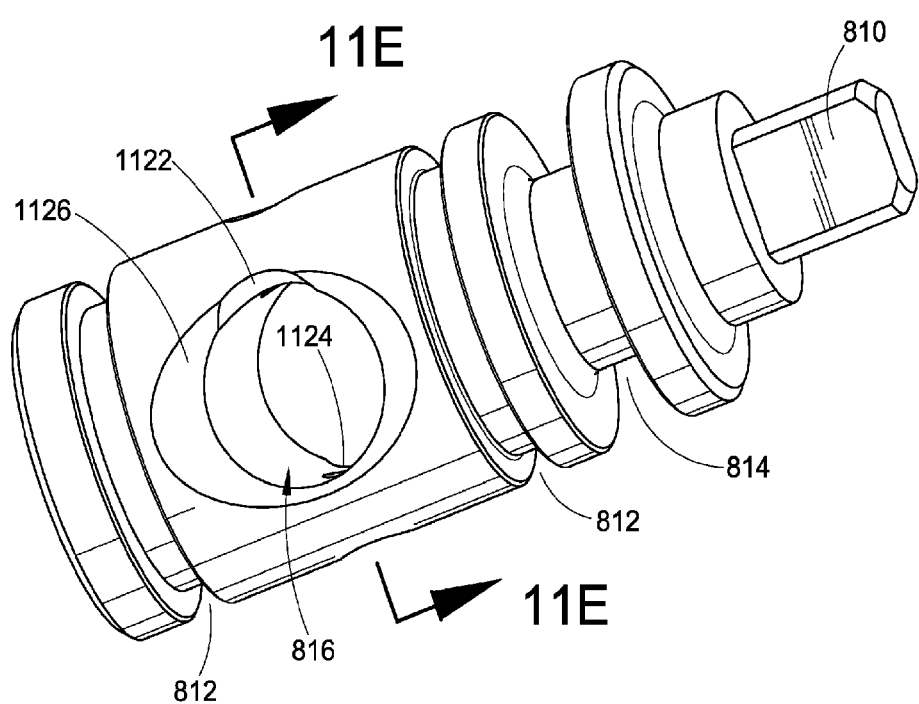
FIG. 11D is a perspective view illustrating an exemplary embodiment of a probe blocking member.
Figure 11E:
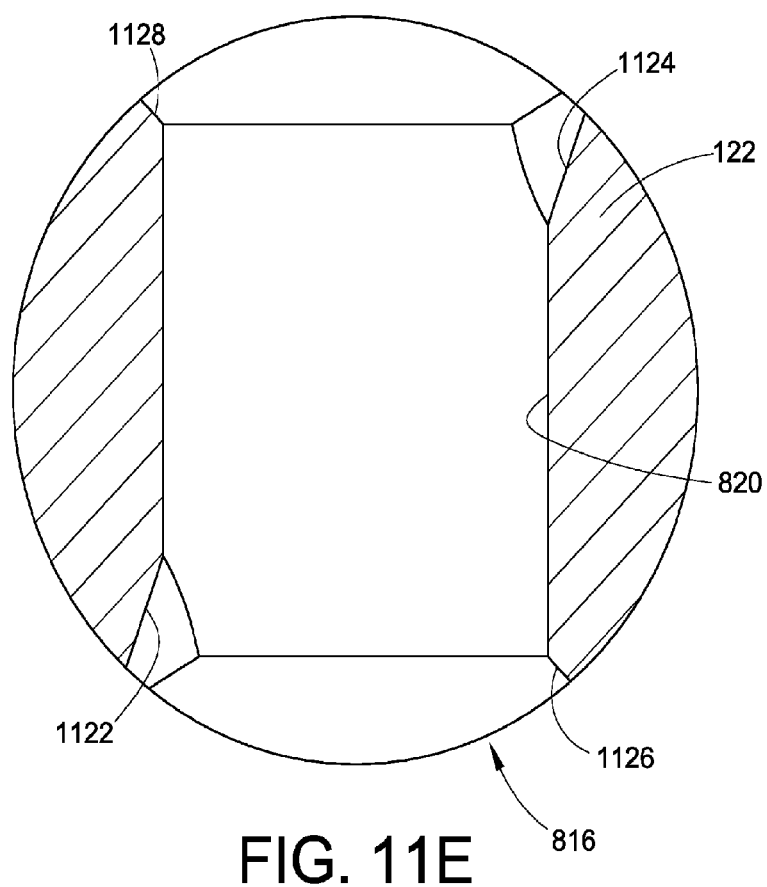
FIG. 11E is a sectional view taken along the plane indicated by lines 11E-11E in FIG. 11D.
Figure 11F:
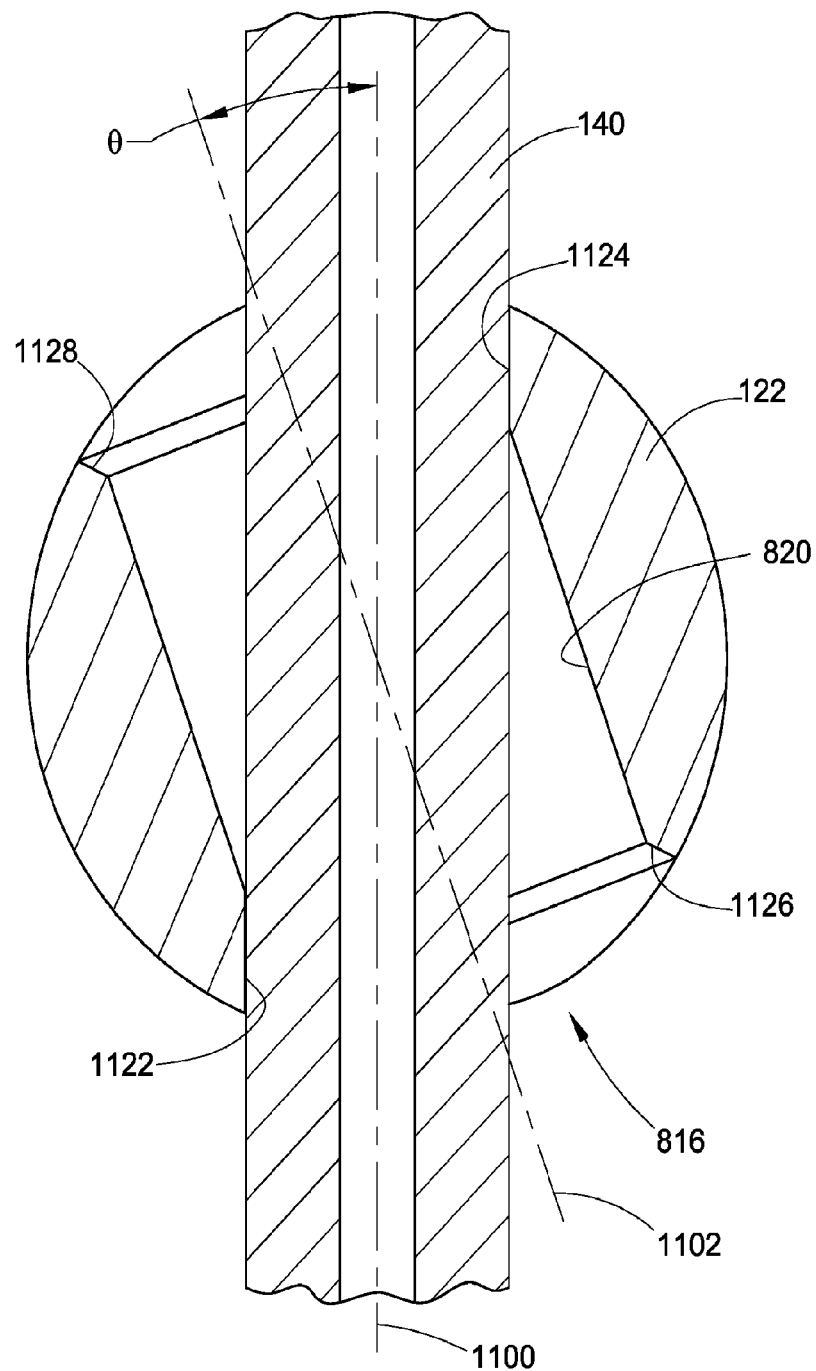
FIG. 11F is a view similar to the view of FIG. 11E showing the probe blocking member turned from a probe accepting position toward a probe blocking position and into engagement with the probe.

Referring to FIGS. 11D-11F, a probe passage 816 may be configured to increase the contact area between the probe blocking member 122 and the probe 140 when the probe blocking device is moved from the probe accepting position toward the probe blocking position and against an inserted probe. In this embodiment, the contact area is increased by providing a probe passage 816 with a central cylindrical bore 820 and first and second notch areas 1122, 1124. The notch areas can take a wide variety of different forms. In one embodiment, the notch areas 1122, 1124 have skewed cylindrical surfaces that match the outside surface of a cylindrical object. For example, the notch areas 1122, 1124 may substantially correspond to an outer cylindrical surface of the probe 140 (see FIG. 11F). However any shape that increases the contact area between the probe 140 and the bore can be used. Referring to FIG. 11F, the illustrated notch areas 1122, 1124 have a common central axis 1100 that is out of alignment with respect to a central axis 1102 of the cylindrical bore 820. For example, an angle θ may be formed between the common central axis of the notch areas 1122, 1124 and the central axis 1102 of the cylindrical bore 820. The notch areas 1122, 1124 increase the contact area between the probe blocking member 122 and the probe 140 as compared to a substantially continuous cylindrical bore to reduce the potential stress applied to the probe. In the embodiment illustrated by FIGS. 11D-11F, the probe passage 816 also includes first and second chamfers 1126, 1128. The first and second chamfers 1126, 1128 help to guide the probe end into the central cylindrical bore 820 during probe insertion and retraction.

Figure 11G:
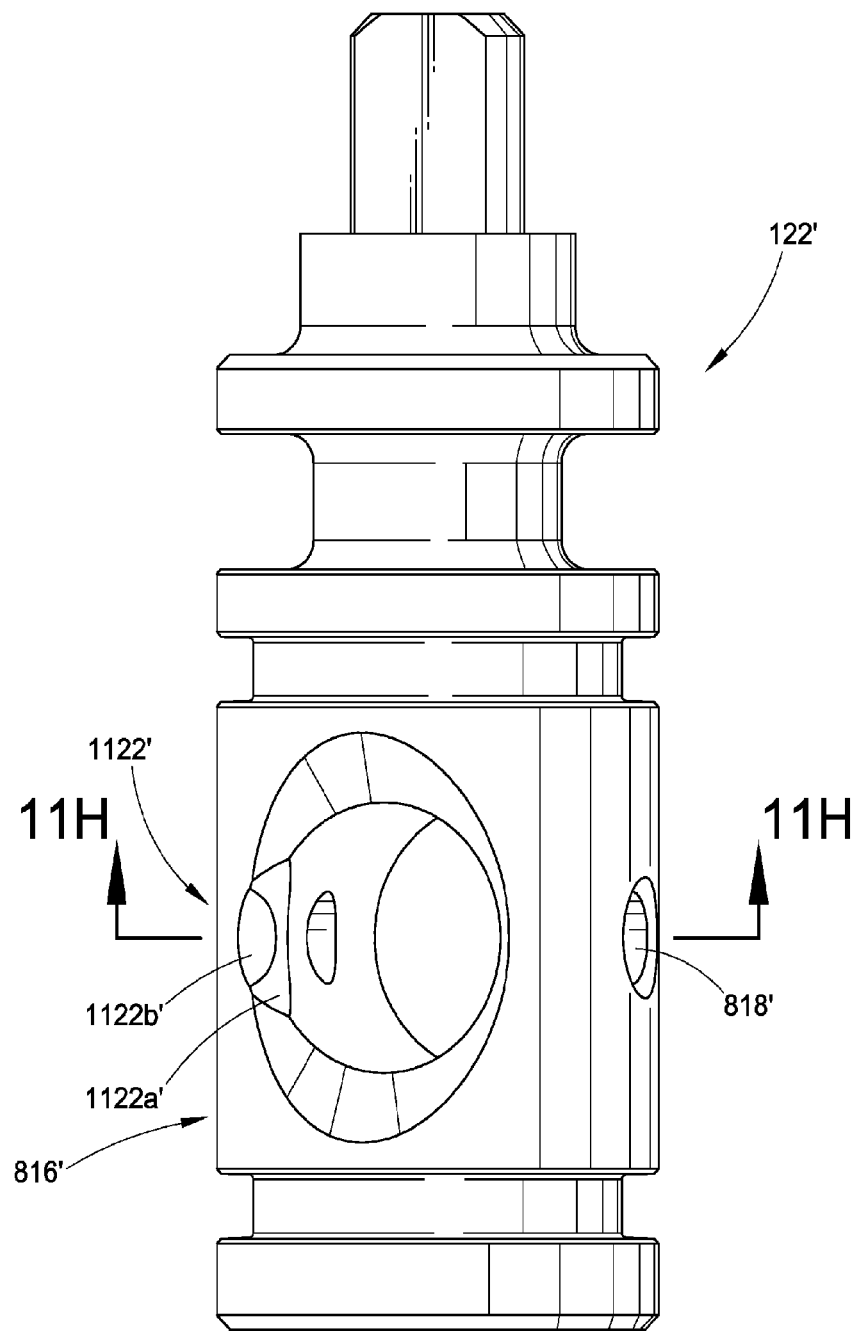
FIG. 11G is a perspective view illustrating an exemplary embodiment of another probe blocking member.
Figure 11H:
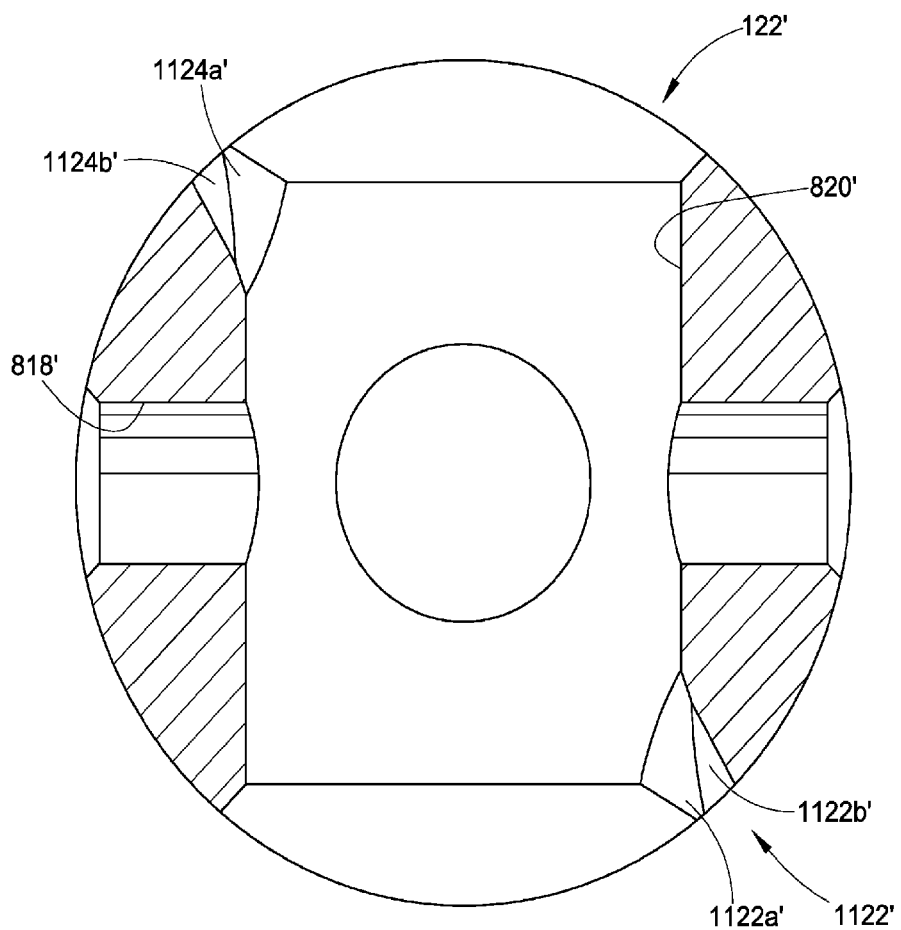
FIG. 11H is a sectional view taken along the plane indicated by lines 11H-11H in FIG. 11G.

In another embodiment, notched areas in the orifice of a probe blocking member may include discontinuous surfaces configured to accommodate probes of multiple sizes. For example, as shown in FIGS. 11G and 11H, a probe blocking member 122' includes a probe passage 816' with a notched area 1122' having a first skewed cylindrical surface 1122a' contoured to correspond with a ⅜" diameter probe, and a second skewed cylindrical surface 1122b' contoured to correspond with a ¼" diameter probe, to allow for an increased contact surface for either size probe. Similar discontinuous skewed cylindrical surfaces may be provided at the opposite end of the central bore 820'.

Other arrangements may be utilized to reduce or eliminate stress applied to the probe (or other insertable element) by the probe blocking member when the probe blocking device is moved from the probe accepting position toward the probe blocking position with the probe inserted into the probe blocking device. For example, a probe blocking member may include a softer or compressible material (e.g., a plastic or elastomer) that transmits less impact force to the inserted probe. As another example, a probe blocking device may be provided with a spring-loaded handle that prevents excessive impact force from being applied to the inserted probe, by deformation of a spring connecting the handle to the probe blocking member. In still other embodiments, a probe blocking device locking arrangement may be utilized to prevent movement of the probe blocking device toward the probe blocking condition when a probe is inserted into the probe blocking device. For example, a sensor may be utilized to detect the presence of a probe in the probe blocking device, and to deliver a signal to an electromechanical locking mechanism to prevent operation of the probe blocking device. As other examples, mechanical or magnetic latches triggered by insertion of the probe may also be used to lock the probe blocking device against movement toward the probe blocking condition.

Referring back to the exemplary embodiment of FIGS. 11A-11C, the handle 800 is coupled to the integral stem 810. The handle 800 is moveable to move the probe blocking member 122 to the probe blocking position (see FIG. 4C) and to the probe accepting position (see FIG. 8). In one exemplary embodiment, the handle 800 is configured to inhibit the application of excessive stress to the probe 140. This can be accomplished in a wide variety of different ways. For example, the handle may be located in an area that is difficult to access when the probe 140 is inserted, the handle may be constructed such that it is difficult to apply a large force to the handle, for example by making the handle short and/or a clutch arrangement may be provided between the handle 800 and the probe blocking member 122. In the illustrated embodiment, the handle 800 in the probe accepting position is positioned behind the block valve handle 180, making it difficult to apply excessive force to the handle 800 when moving it from the probe accepting position toward the probe blocking position (see FIG. 7). In addition, the handle 800 is significantly shorter than the handle of the block valve 106.

To facilitate venting of the valve assembly and downstream tubing volume when the block valve 106 is closed and the bleed valve 108 is open, vent holes 818 may be provided in the probe blocking member 122, as shown in FIG. 11C. The vent holes 818 may extend substantially perpendicular to the probe passage 816. The holes may be sized to be small enough to not allow passage of a probe (for example, smaller than ¼" in diameter), and large enough to readily vent the assembly.

Referring to FIGS. 11A and 11B, the probe blocking member 122 is disposed in a cylindrical bore 850. Referring to FIG. 4C, the cylindrical bore 850 intersects the fluid access passage 104 in the valve body 102. The seal rings 802 are disposed in the seal recesses 812. The seal rings 802 seal against the valve body 102 and the probe blocking member 122. The seal rings 802 prevent process fluid in the process fluid passage 104 from exiting the valve body 102. The seal rings 802 may be o-ring style seal rings. In the illustrated embodiment, the probe blocking member 122 does not function as a valve that completely prevents fluid from passing from the block valve 106 side of the probe blocking member to the probe port 118 side of the probe blocking member. As indicated above, the probe blocking device 110 can be changed to a shutoff valve configuration if sealing between the block valve side to the probe port side is required.

Referring to FIGS. 11A and 11B, the probe blocking member 122 is retained in the cylindrical bore 850 by the retention pin 804. The retention pin 804 is secured in a retention pin bore 870 in the valve body 102 and extends into the annular retention recess 814 in the probe blocking member 122 (see FIG. 11B). The retention pin 804 allows rotational movement of the blocking member 122 in the cylindrical bore 850 about an axis 880. The retention pin 804 inhibits movement of the probe blocking member 122 in the cylindrical bore 850 in the direction of the axis 880.

In the illustrated embodiment, the probe blocking device 110 is limited to ninety degrees of rotation between the probe accepting position (see FIGS. 7 and 8) and the probe blocking position (see FIGS. 4B and 4C). This can be accomplished in a wide variety of different ways. In the illustrated embodiment, stop pins 302 are disposed in the valve body 102. The stop pins 302 are positioned to engage the probe blocking device handle at the probe blocking position and at the probe accepting position.

The bleed valve 108 may take a wide variety of different forms. Examples of different types of valves that may be used include, but are not limited to, ball valves, plug valves, shuttle valves, needle valves, and the like. Any type of valve capable of opening and closing the bleed passage 150 can be used. The illustrated bleed valve 108 is substantially identical to the block valve, and therefore is not described again in detail.

Figure 10A:
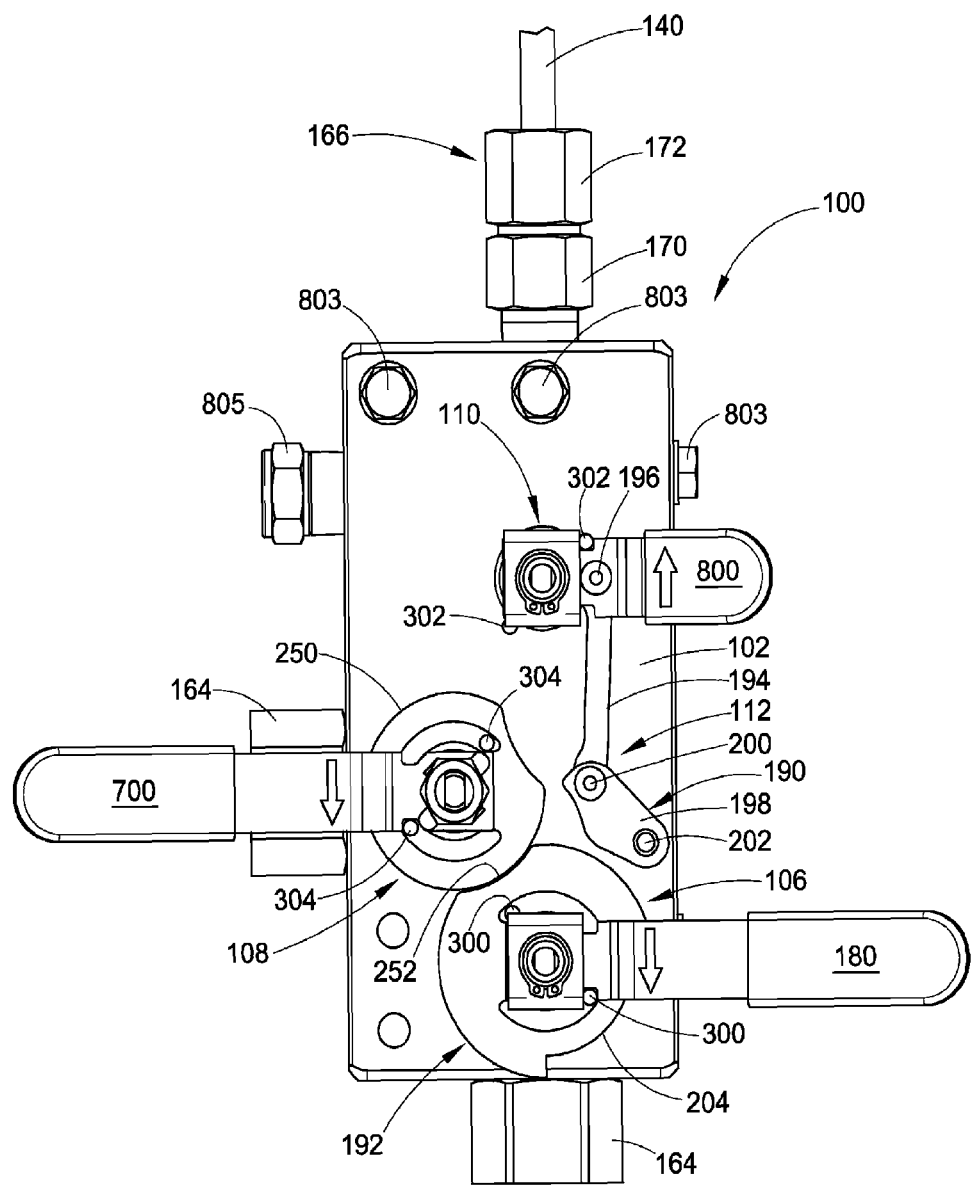
FIG. 10A is a front view of a process interface valve assembly, illustrating a bleed valve moved from a closed position to an open position.
Figure 10B:
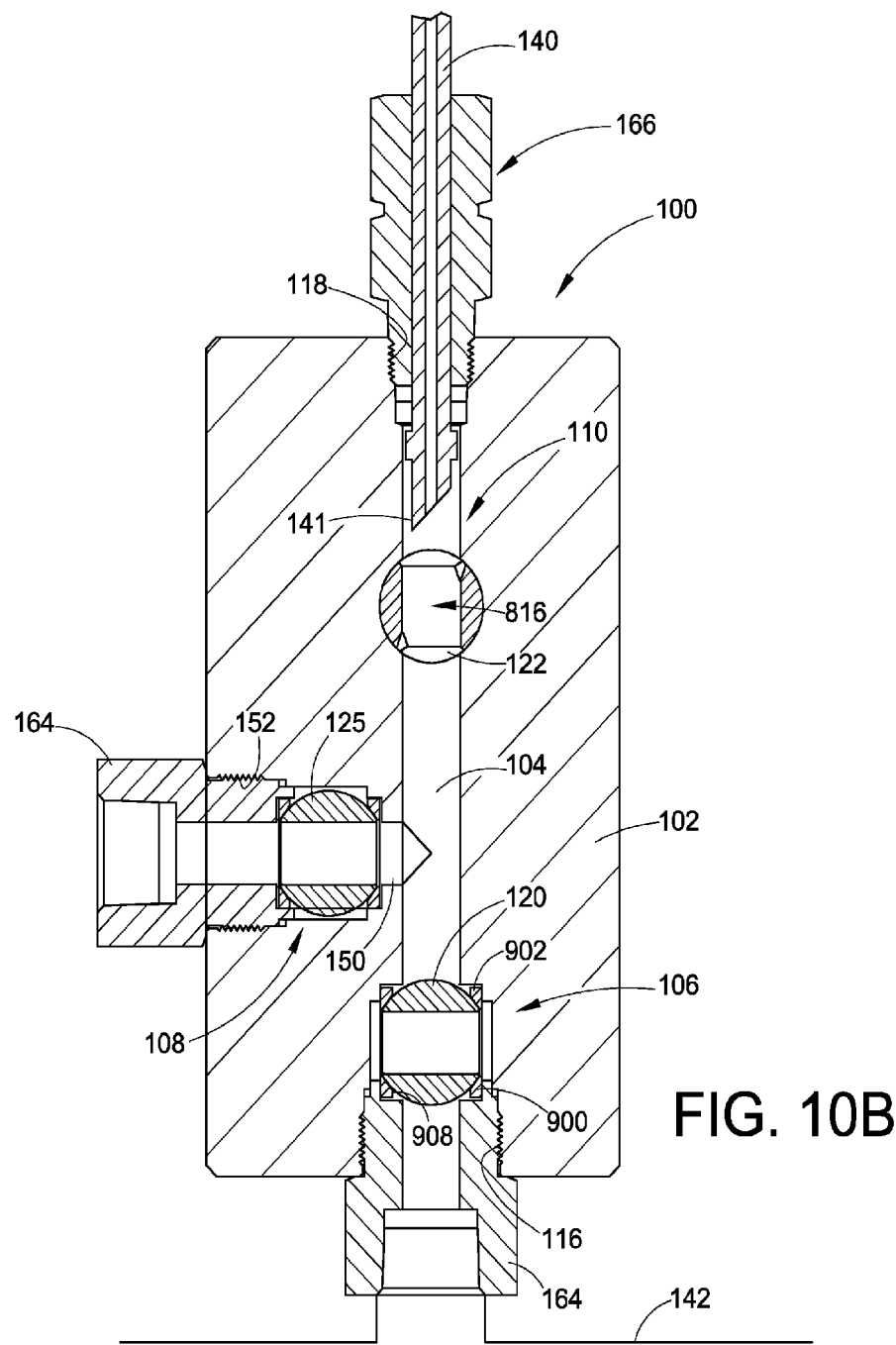
FIG. 10B is a sectional view of the process interface valve assembly shown in FIG. 10A.

In the illustrated embodiment, the bleed valve 108 is limited to ninety degrees of rotation between the closed position (see FIGS. 4B and 4C) and the open position (see FIGS. 10A and 10B). This can be accomplished in a wide variety of different ways. In the illustrated embodiment, stop pins 304 are disposed in the valve body 102. The stop pins 304 are positioned to engage a bleed valve handle 700 at the open and closed positions.

The valve interlock arrangement 112 can take a wide variety of different forms. The valve interlock arrangement 112 may take any form that prevents the block valve 106 from being moved to the closed position when the probe blocking device 110 is in the probe accepting position. Additionally or alternatively, the valve interlock arrangement 112 may take any form that prevents the probe blocking device from being moved from the probe blocking position to the probe accepting position when the block valve 106 is closed. In one exemplary embodiment, the valve interlock arrangement 112 is configured to prevent an amount of movement of the block valve 106 from the open position toward the closed position from reaching an amount that would damage the probe 140. In another exemplary embodiment, the valve interlock arrangement 112 is configured to prevent substantially all movement of the block valve 106 from the open position toward the closed position when the probe blocking device is in the probe accepting position. Additionally, as illustrated, the valve interlock 112 may be visible from the outside of the valve assembly. By making the interlock visible, a user will more readily recognize that the valve interlock 112 is working properly, rather than thinking there is a problem with the valve assembly.

In one embodiment, a valve interlock arrangement may include an access stop member coupled with an access blocking or probe blocking device, and a valve stop member coupled with a block valve or other such flow control valve. According to an aspect of the present application, the valve interlocking arrangement may be configured such that when the valve is in the open condition and the access blocking device is in the access palliating condition, the access stop member is positioned to impede movement of the valve (for example, by obstructing movement of the valve stop member) and thereby prevent the valve from being moved to the closed condition. In an exemplary embodiment, the access stop member includes a linkage coupled to the access blocking device, with a first link pivotally connected to a handle of the access blocking device and a second link pivotally connected to the first link and pivotally connected to the valve body. When the valve is in the open condition and the access blocking device is in the access permitting condition, the second link is positioned to obstruct movement of the valve stop member and thereby prevent the valve from being moved to the closed condition.

In the illustrated embodiment, the valve interlock arrangement 112 includes the probe blocking device 110, a linkage 190 coupled to the probe blocking device 110, and a block valve disk 192 coupled to the block valve 106. In this embodiment, the block valve interface component 32 (see FIG. 1A) is the block valve disk 192, the probe interface component 30 (see FIG. 1A) is the probe blocking device 110 and the linkage 190 links the two together. Referring to FIG. 4B, the linkage 190 comprises a first link 194 pivotally connected to the handle 800 of the probe blocking device 110 at a first pivot point 196 and a second link 198 pivotally connected to the first link 194 at a second pivot point 200 and pivotally connected to the valve body 102 at a third pivot point 202. Referring to FIG. 7, the block valve disk 192 includes a recess 204 with a stop surface 206. Referring to FIG. 4B, when the probe blocking device 110 is in the probe blocking position, the second link 198 is spaced apart from the block valve disk 192. Referring to FIG. 7, when the block valve 106 is in the open position and the probe blocking device 110 is in the probe accepting position, the second link 198 is positioned in the recess 204 adjacent to the stop surface 206 to prevent the block valve 106 from being moved to the closed position.

According to another aspect of the present application, a valve interlocking arrangement may additionally or alternatively be configured such that when the valve is in the closed condition and the access blocking device is in the access blocking condition, the valve stop member is positioned to impede movement of the access blocking device (for example, by obstructing movement of the access stop member) and thereby prevent the access blocking device from being moved to the access permitting condition. Such an arrangement may be utilized to prevent insertion of a probe or other element through the access blocking device and against the closed valve (which could cause damage to the inserted element or to the valve). In an exemplary embodiment, the access stop member includes a linkage coupled to the access blocking device, with a first link pivotally connected to a handle of the access blocking device and a second link pivotally connected to the first link and pivotally connected to the valve body. When the valve is in the closed condition and the access blocking device is in the access blocking condition, the valve stop member is positioned to obstruct movement of the second link and thereby prevent the access blocking device from being moved to the access permitting condition.

Figure 5:
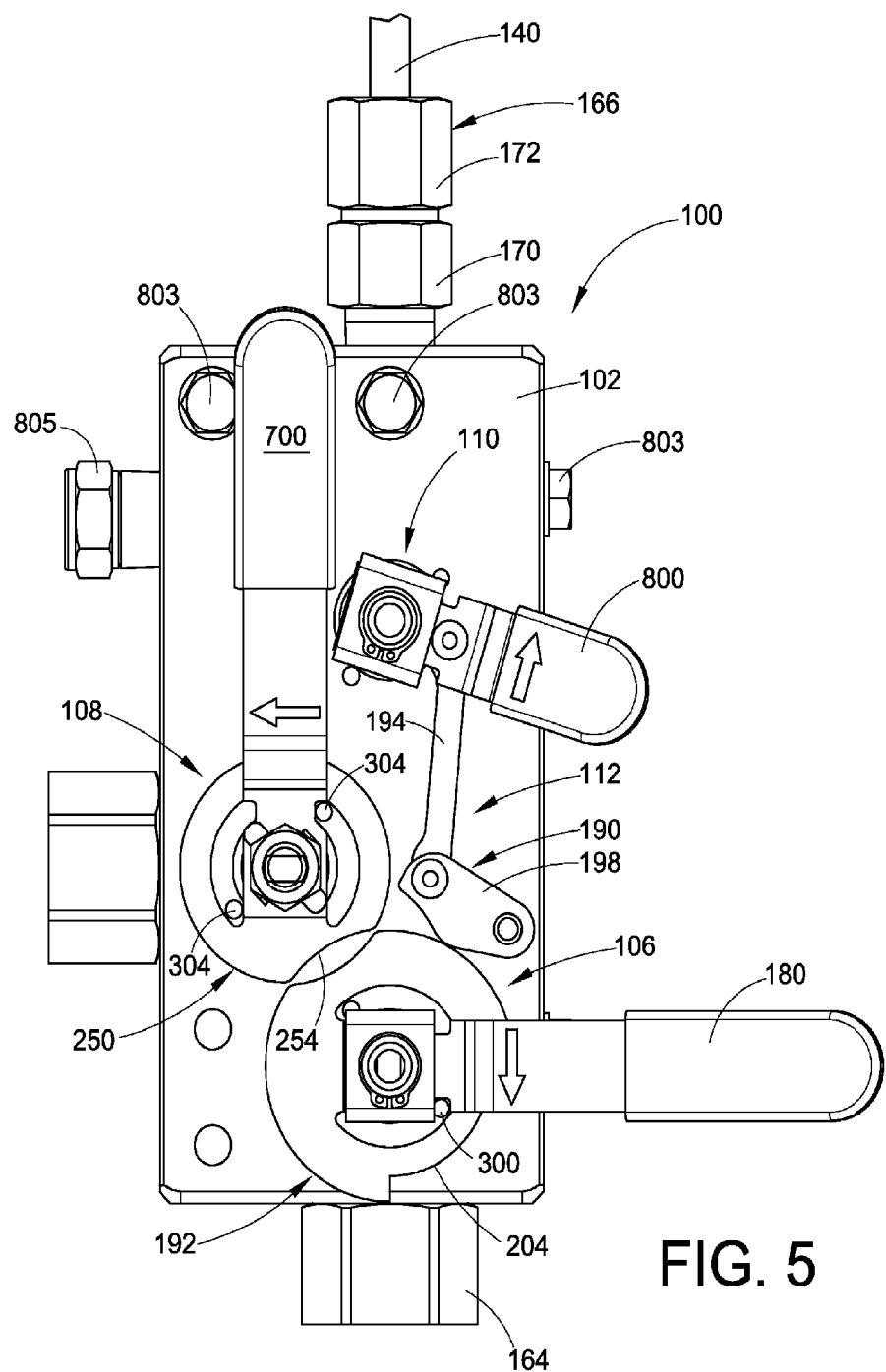
FIG. 5 is a view of the process interface valve assembly illustrating a probe blocking device being moved from a probe blocking position toward a probe accepting position.

FIG. 5 illustrates that when the block valve 106 of the illustrated assembly is closed, the recess 204 is not aligned with the second link 198. When the probe blocking device 110 is moved from the probe blocking position toward the probe accepting position, the second link 198 engages the disk 192. The engagement between the second link 198 and the disk 192 prevents the probe blocking device 110 from being moved to the probe accepting position when the block valve 106 is closed.

According to another aspect of the present application, in a valve assembly including a first valve (such as a block valve) and a second valve (such as a bleed valve), a valve interlock arrangement may additionally or alternatively be configured such that when the first valve is in the open condition, the second valve is prevented from being moved to the open condition. Still further, the valve interlock arrangement may additionally or alternatively be configured such that when the second valve is in the open condition, the first valve is prevented from being moved to the open condition.

As illustrated, when a bleed valve 108 is included, the valve interlock arrangement 112 may optionally be configured such that the bleed valve 108 is prevented from being opened when the block valve 106 is open (FIG. 6A) and/or the block valve 106 is prevented from being opened when the bleed valve is open (FIG. 10B). This can be accomplished in a wide variety of different ways. For example, any mechanical linkage, stop, etc. can be used to prevent one valve from being opened when the other valve is opened. In one such embodiment, a valve stop member is coupled to the block valve, and a bleed stop member is coupled to the bleed valve. When the block valve is open, the valve stop member is positioned to impede movement of the bleed valve (for example, by obstructing movement of the bleed stop member) and thereby prevent the bleed valve from being moved to the open condition. Additionally or alternatively, the valve interlocking arrangement may be configured such that when the bleed valve is open, the bleed stop member may be positioned to impede movement of the block valve (for example, by obstructing movement of the valve stop member) and thereby prevent the block valve from being moved to the open condition.

In the illustrated embodiment, the disk 192 and a disk 250 that is coupled to the bleed valve 108 are configured to prevent the bleed valve 108 from being opened when the block valve 106 is open and to prevent the block valve 106 from being opened when the bleed valve 108 is open. Referring to FIG. 4B, the block valve disk 192 includes a recess 252 and the bleed valve disk 250 includes a recess 254. (In the embodiment of FIG. 13, where a bleed valve is not included, the recess need not be included in the block valve disk.) The recess 252 of the block valve disk 192 has a shape that is complimentary to the shape of the perimeter of the bleed valve disk 250. The recess 254 of the bleed valve disk 250 has a shape that is complimentary to the shape of the perimeter of the block valve disk 192.

Referring to FIG. 4B, the recesses 252, 254 are adjacent to one another, such that when both the block valve 106 and the bleed valve 108 are in the closed position, either the block valve or the bleed valve (but not both) can be moved to the open position (see FIGS. 6A and 10A). Referring to FIG. 6A, when the block valve 106 is in the open position, the perimeter of the block valve disk 192 is disposed in the recess 254 of the bleed valve 108. As a result, the bleed valve 108 is prevented from being moved from the closed position to the open position. Referring to FIG. 10A, when the bleed valve 108 is in the open position, the perimeter of the bleed valve disk 250 is disposed in the recess 252 disk 192. As a result, the block valve 106 is prevented from being moved from the closed position to the open position.

FIGS. 4A-10B illustrate operation of the process interface valve assembly 100. FIGS. 4A-4C illustrate the process interface valve assembly 100 with the block valve 106 closed, the bleed valve 108 closed, and the probe blocking device 110 in the probe blocking position. Referring to FIG. 4C, the block valve 106 prevents fluid from flowing into the fluid access passage 104, the bleed valve 108 prevents fluid from flowing out through the bleed port 152, and the probe blocking device 110 prevents the probe from being inserted into contact with the valve element 120 of the block valve 106.

Referring to FIG. 5, the valve interlock arrangement 112 prevents the probe blocking device 110 from being moved to the probe accepting position when the block valve 106 is closed. This protects the block valve element 120 from being damaged by insertion of the probe 140 into contact with the block valve member when the block valve 106 is closed. In the illustrated embodiment, the second link 198 of the linkage 190 contacts the perimeter of the disk 192 to prevent the probe blocking device from being moved to the probe accepting position when the block valve 106 is closed.

Figure 6B:
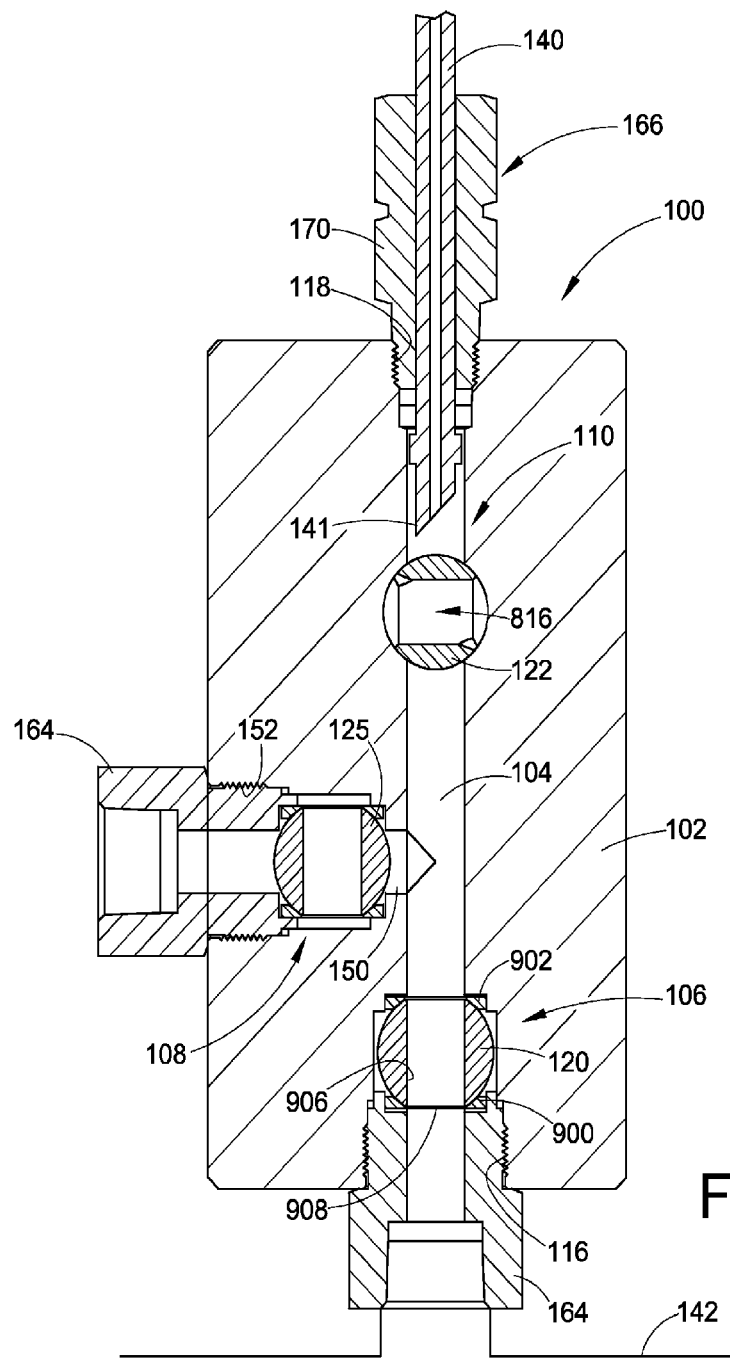
FIG. 6B is an enlarged sectional view of the process interface valve assembly shown in FIG. 6A.

FIGS. 6A and 6B illustrate the block valve 106 opened, with the bleed valve 108 closed, and the probe blocking device 110 in the probe blocking position. Referring to FIG. 6B, the open block valve 106 now allows fluid to flow into the fluid access passage 104. The probe fitting 166 prevents fluid from leaking around the probe 140. The probe valve 143 (FIG. 4A) may be closed to prevent any fluid that flows past the probe blocking device 110 from exiting the probe. The closed bleed valve 108 prevents fluid from flowing out through the bleed port 152. The bleed valve 108 is prevented from being opened by the valve interlock assembly 112. That is, the perimeter of the disk 192 is disposed in the recess 254 of the second disk 250 to prevent the bleed valve 108 from being opened. The probe blocking device 110 in the probe blocking position prevents the probe from being inserted into fluid access passage 104 and through the opened block valve 106.

FIGS. 7 and 8 illustrate the probe blocking device 110 moved to the probe accepting position, with the block valve 106 opened, and the bleed valve 108 closed. Referring to FIG. 8, the probe blocking member 122, now in the probe accepting position, is open for insertion of the probe 140. Referring to FIG. 7, the block valve 106 is prevented from being closed by the valve interlock assembly 112. That is, the second link 198 of the linkage 190 is disposed in the recess 204 of the disk 192 adjacent to the stop surface 206 to prevent the block valve 106 from being closed.

FIG. 8 illustrates the probe 140 inserted, with the probe blocking device 110 in the probe accepting position, the block valve 106 opened, and the bleed valve 108 closed. The probe valve 143 can be opened to sample fluid from the process fluid vessel 142 (FIG. 8) or conduit through the probe 140. The block valve 106 is prevented from being closed by the valve interlock assembly 112 to prevent the probe 140 from being damaged.

Figure 14A:
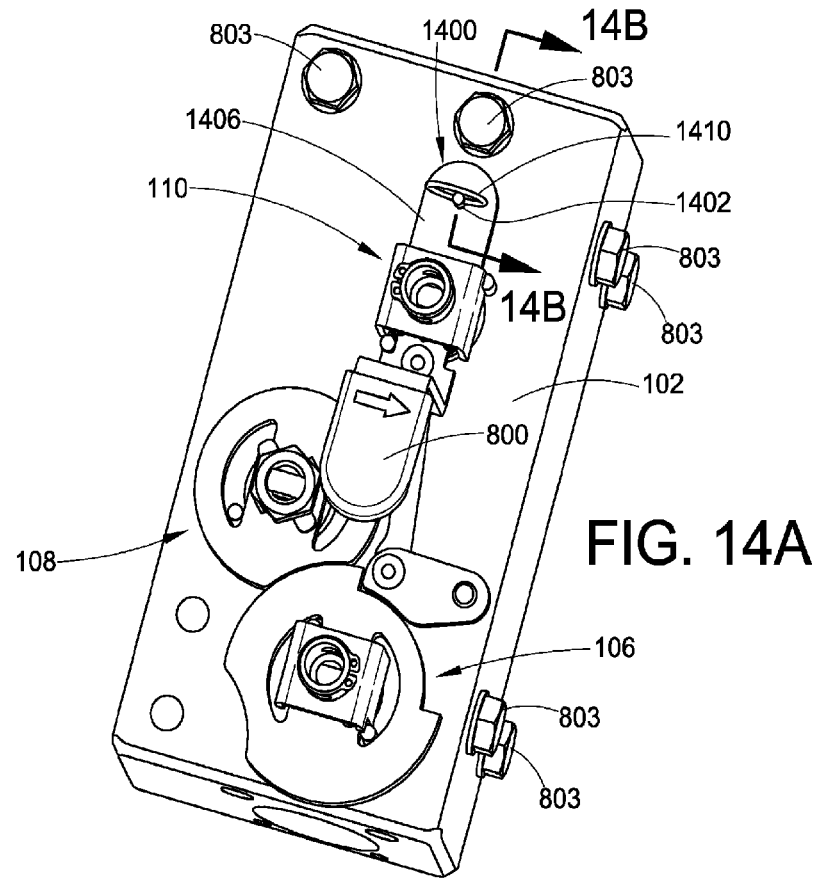
FIG. 14A is a perspective view of a process valve assembly with a probe blocking assembly having a locking mechanism (handles of the block valve and the bleed valve are removed)
Figure 14B:
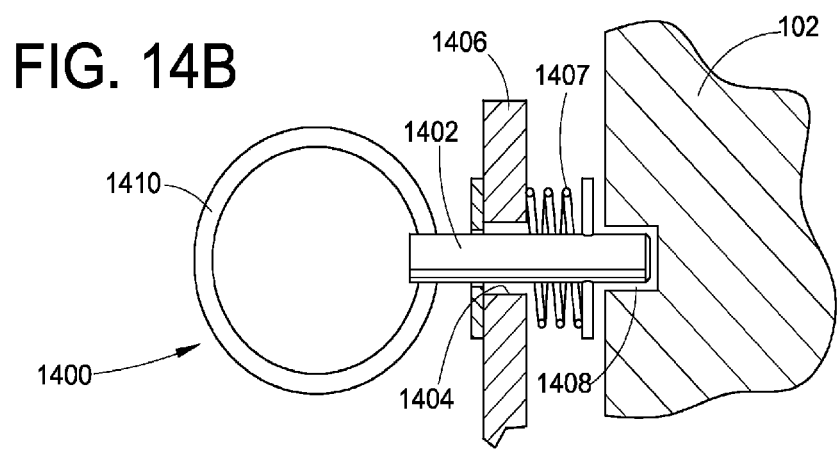
FIG. 14B is a schematic illustration of the locking mechanism shown in FIG. 14A as indicated by section lines 14B-14B in FIG. 14A.

In one embodiment, an optional locking arrangement may be added to the probe blocking device 110 that would prevent the probe blocking device from being moved from the probe accepting position to the probe blocking position when the probe is inserted. The locking mechanism can take a wide variety of different forms. For example, any arrangement for locking the probe blocking device handle 800 to the block valve handle 180 or the valve body 102 can be used. FIGS. 14A and 14B illustrate one example of the wide variety of acceptable locking mechanisms. In the example, a locking mechanism 1400 comprises a spring loaded pin 1402. The pin 1402 is mounted in a hole 1404 in an extension 1406 of the probe blocking device handle 800. A spring 1407 biases the pin 1402 into a recess 1408 in the valve body 102 to lock the extension 1406 of the handle 800 to the valve body. The pin 1402 is pulled out of the recess 1408 against the biasing force of the spring 1407 (for example by pulling attached ring 1410) to unlock the mechanism 1400. When the mechanism 1400 is unlocked, the probe blocking device can be moved from the probe accepting position to the probe blocking position. As such, the valve operator is required to perform two steps (i.e. pull the pin and turn the handle) to move the probe blocking device 110 to the probe blocking position. This two step process reduces the likelihood that an operator will inadvertently move the probe blocking device 110 toward the probe blocking position while the probe 140 is in the probe blocking device.

Figure 9:
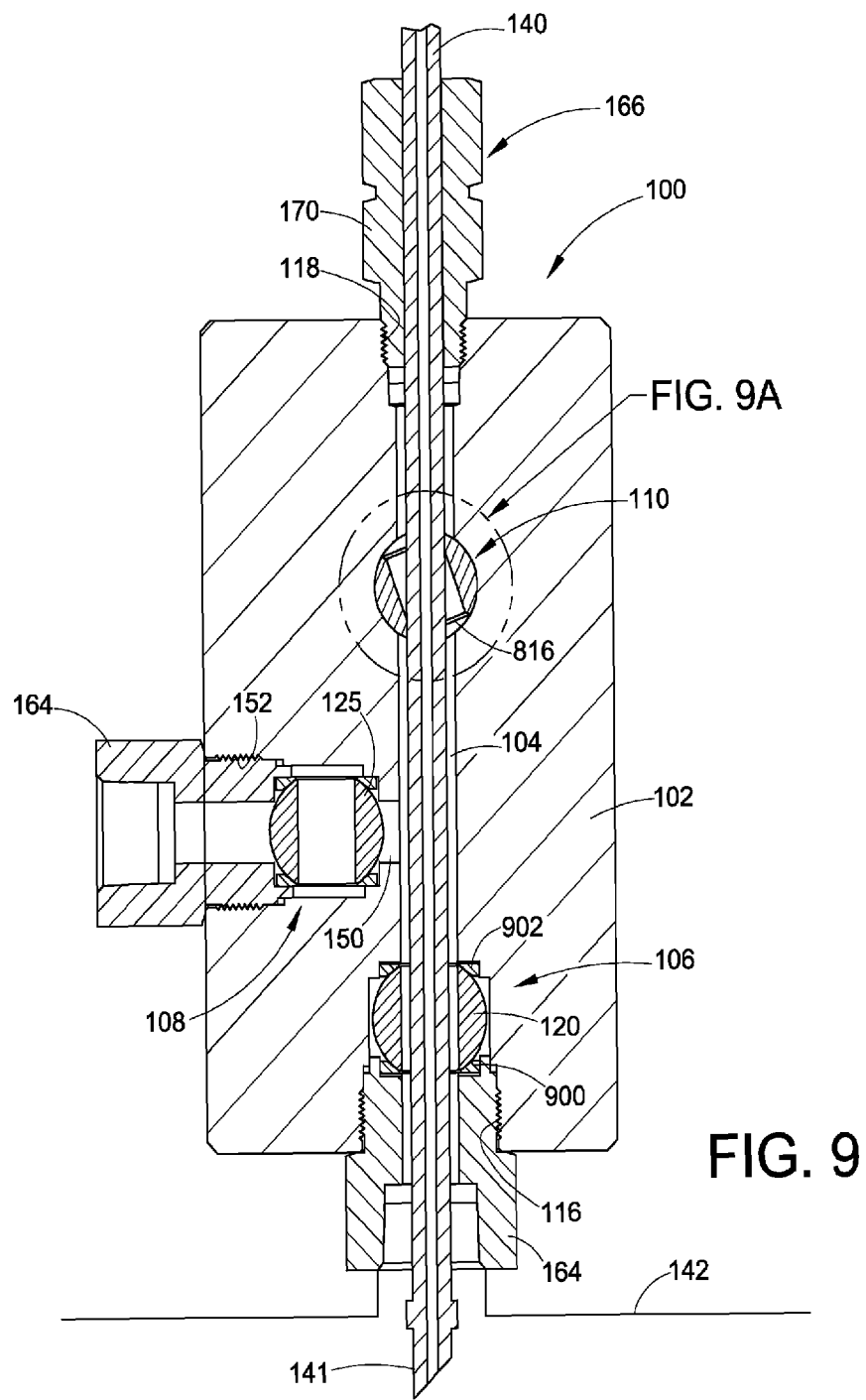
FIG. 9 is a sectional view similar to FIG. 8 illustrating the probe blocking device moved from the probe accepting position toward the probe blocking position.
Figure 9A:
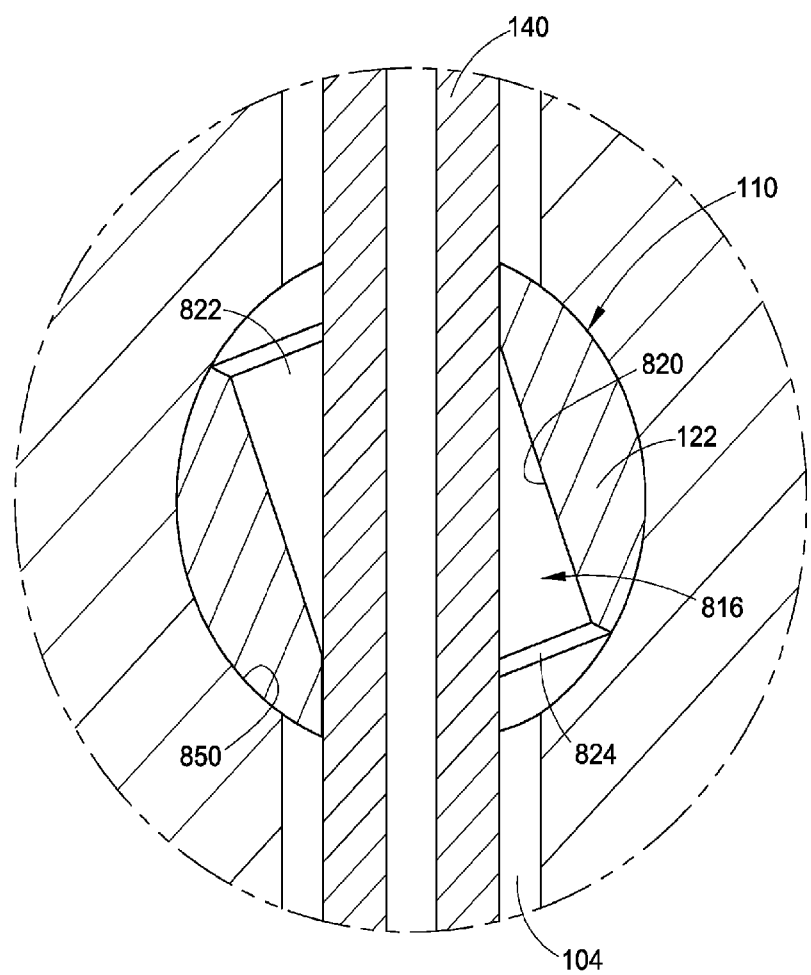
FIG. 9A is an enlarged portion of FIG. 9 as indicated by reference 9A in FIG. 9.

FIGS. 9 and 9A illustrate the probe blocking device 110 moved from the probe accepting position toward the probe blocking position, with the probe 140 inserted, the block valve 106 opened, and the bleed valve 108 closed, as in FIGS. 8A-8B. Referring to FIGS. 9B and 9C, the first and second conical portions 822, 824 contact the probe 140 over a large contact area to reduce the stress applied to the probe.

The probe 140 can be retracted out of the block valve 106 and out of the probe blocking device 110 when the components of the valve assembly 100 are in the positions illustrated by FIGS. 7 and 8. Once the probe 140 is retracted out of the probe blocking device 110, the probe blocking device 110 can be returned to the probe blocking position, as illustrated by FIGS. 4A and 6B. Once the probe blocking device 110 is in the probe blocking position, the block valve 106 can be closed, as illustrated by FIGS. 4A-4C.

Referring to FIGS. 10A and 10B, after the block valve 106 is closed, the bleed valve can be opened to remove process fluid in the valve assembly 100, in the probe 140, and or in any instrumentation that is coupled to the probe. The block valve 106 is prevented from being opened by the valve interlock assembly. That is, the perimeter of the disk 250 is disposed in the recess 252 of the first disk 192 to prevent the block valve 106 from being opened. The probe blocking device 110 is in the probe blocking position to prevent the probe from being inserted into the fluid access passage 104 and into contact with the block valve 106. After any process fluid is removed through the bleed valve 108, the bleed valve can be closed to return the valve assembly to the condition illustrated by FIGS. 4A-4C.

The valves 106, 108, and the probe blocking device 110 can be arranged in the valve body 102 in a wide variety of different positions. In the illustrated embodiment, the handles of the valves 106, 108, and the probe blocking device 110 are all on the same side of the valve body. This provides a visual indication of the state of both valves and the probe blocking device and makes operation of the valve assembly easy.

Still other features and components may be provided with one or more of the valve assemblies described herein. For example, the valve body 102 may be provided with threaded mounting holes and cap screws 803 or other such fasteners, to facilitate the assembly of mounting brackets, lockout brackets, heating elements, or other such components. As another example, the valve body may be provided with a port for installation of a sensor or gage, such as a thermometer, to monitor the condition of the fluid within the valve body 102. This port may be blocked, for example, using a pipe plug 805, when not in use.

The invention has been described with reference to the preferred embodiments. Modifications and alterations will occur to others upon a reading and understanding of this specification.

I claim:

1. A valve assembly comprising: a valve body having a process fluid access passage extending through the valve body from a process fluid port to an access port; a block valve disposed in the fluid access passage, said block valve being operable between open and closed conditions; and an access blocking device disposed in the process fluid access passage between the access port and the block valve, the access blocking device being moveable from an access blocking condition in which access to the block valve through the access port is blocked, to an access permitting condition in which access to the block valve through the access port is permitted;

wherein the access blocking device includes an internal passage comprising a central cylindrical bore and first and second notches intersecting bore edges at opposite ends of the internal passage, wherein the first and second notches provide an increased contact area between the access blocking device and a probe inserted through the central cylindrical bore.

2. The valve assembly of claim 1, wherein the block valve is configured to allow a probe to be inserted through the process fluid port when the block valve is in the open condition.

3. The valve assembly of claim 1, wherein the first and second notches each include cylindrical surfaces sized and oriented to correspond to an outer cylindrical surface of an inserted probe.

4. The valve assembly of claim 1, wherein the first and second notches each include a first surface sized and oriented to correspond to an outer cylindrical surface of a first probe, and a second surface discontinuous with the first cylindrical surface and sized and oriented to correspond to an outer surface of a second probe, with the outer surface of the second probe being dimensionally different than the outer surface of the first probe.

5. The valve assembly of claim 1, further comprising a bleed passage defined in the valve body and extending from a bleed port to the fluid access passage, and a bleed valve disposed in the bleed passage between the bleed port and the fluid access passage, the bleed valve being operable between an open condition and a closed condition.

6. The valve assembly of claim 1, further comprising a valve interlock arrangement configured such that operability of one of the block valve and the probe blocking device is a function of an operational state of the other of the block valve and the probe blocking device.

7. The valve assembly of claim 6, wherein the block valve is prevented from being moved to the closed condition when the access blocking device is in the access permitting condition.

8. The valve assembly of claim 6, wherein the access blocking device is prevented from being moved to the access permitting condition when the block valve is in the closed condition.

9. A valve assembly comprising:
a valve body having a process fluid access passage extending through the valve body from a process fluid port to an access port;
a block valve disposed in the fluid access passage, said block valve being operable between open and closed conditions; and
an access blocking device disposed in the process fluid access passage between the access port and the block valve, the access blocking device being moveable from an access blocking condition in which access to the block valve through the access port is blocked, to an access permitting condition in which access to the block valve through the access port is permitted; and a valve interlock arrangement configured such that operability of one of the block valve and the probe blocking device is a function of an operational state of the other of the block valve and the probe blocking device;

wherein the valve interlock arrangement comprises an access stop member coupled to the access blocking device and a valve stop member coupled to the block valve, wherein when the block valve is in the open condition and the access blocking device is in the access permitting condition, the access stop member is positioned to engage the valve stop member and thereby prevent the block valve from being moved to the closed condition; and wherein the access stop member comprises a linkage coupled to the access blocking device, with a first link connected to and pivotable with respect to a handle of the access blocking device and a second link having a first portion connected to and pivotable with respect to the first link and a second portion connected to and pivotable with respect to the valve body, wherein when the block valve is in the open condition and the access blocking device is in the access permitting condition, the second link is positioned to engage the valve stop member and thereby prevent the block valve from being moved to the closed condition.

10. The valve assembly of claim 9, wherein the access blocking device includes an internal passage comprising a central cylindrical bore and first and second notches at opposite ends of the internal passage.

11. The valve assembly of claim 10, wherein the first and second notches provide an increased contact area between the access blocking device and a probe inserted through the central cylindrical bore to reduce said stress applied to the probe when the access blocking device is moved from the access permitting position toward the access blocking position and into contact with the probe.

12. The valve assembly of claim 9, wherein the valve stop member comprises a plate connected to a handle of the block valve for rotation therewith.

13. The valve assembly of claim 9, wherein when the block valve is in the closed condition and the access blocking device is in the access blocking condition, the valve stop member is positioned to block movement of the second link and thereby prevent the access blocking device from being moved to the access permitting condition.

14. The valve assembly of claim 9, wherein the block valve is configured to allow a probe to be inserted through the process fluid port when the block valve is in the open condition.

15. The valve assembly of claim 9, further comprising a bleed passage defined in the valve body and extending from a bleed port to the fluid access passage, and a bleed valve disposed in the bleed passage between the bleed port and the fluid access passage, the bleed valve being operable between an open condition and a closed condition.

16. A valve assembly comprising:

a valve body having a process fluid access passage extending through the valve body from a process fluid port to an access port and a bleed passage defined in the valve body and extending from a bleed port to the fluid access passage;

a block valve disposed in the fluid access passage, said block valve being operable between open and closed conditions;

a bleed valve disposed in the bleed passage between the bleed port and the fluid access passage, the bleed valve being operable between an open condition and a closed condition;

an access blocking device disposed in the process fluid access passage between the access port and the block valve, the access blocking device being moveable from an access blocking condition in which access to the block valve through the access port is blocked, to an access permitting condition in which access to the block valve through the access port is permitted; and a valve interlock arrangement configured such that operability of one of the block valve and the probe blocking device is a function of an operational state of the other of the block valve and the probe blocking device;

wherein the valve interlock arrangement is further configured such that the bleed valve is prevented from being opened when the block valve is in the open condition, and the block valve is prevented from being opened when the bleed valve is in the open condition.

17. The valve assembly of claim 16, wherein the block valve is prevented from being moved to the closed condition when the access blocking device is in the access permitting condition.

18. The valve assembly of claim 16, wherein the access blocking device is prevented from being moved to the access permitting condition when the block valve is in the closed condition.

19. The valve assembly of claim 16, wherein the valve interlock arrangement comprises an access stop member coupled to the access blocking device and a valve stop member coupled to the block valve, wherein when the block valve is in the open condition and the access blocking device is in the access permitting condition, the access stop member is positioned to engage the valve stop member and thereby prevent the block valve from being moved to the closed condition.

20. The valve assembly of claim 16, wherein the valve interlock arrangement comprises a valve stop member coupled to the block valve, and a bleed stop member coupled to the bleed valve, wherein when the block valve is open, the valve stop member is positioned to engage the bleed stop member and thereby prevent the bleed valve from being moved to the open condition.

21. The valve assembly of claim 16, wherein the valve interlock arrangement comprises a valve stop member coupled to the block valve, and a bleed stop member coupled to the bleed valve, wherein when the bleed valve is open, the bleed stop member is positioned to engage the valve stop member and thereby prevent the block valve from being moved to the open condition.

22. The valve assembly of claim 16, wherein the valve stop member comprises a plate connected to a handle of the block valve for rotation therewith.

23. The valve assembly of claim 16, wherein the bleed stop member comprises a plate connected to a handle of the block valve for rotation therewith.

* * * * *